United States Patent [19]

Ivory et al.

[11] Patent Number: 5,298,143
[45] Date of Patent: Mar. 29, 1994

[54] ELECTROPHORETIC PROCESSING

[75] Inventors: Cornelius F. Ivory; William A. Gobie, both of Pullman, Wash.

[73] Assignee: Washington State University Research Foundation, Pullman, Wash.

[21] Appl. No.: 3,979

[22] Filed: Jan. 15, 1993

Related U.S. Application Data

[63] Continuation-in-part of Ser. No. 782,692, Oct. 25, 1991, Pat. No. 5,200,050.

[51] Int. Cl.⁵ .................. G01N 27/26; G01N 27/447; B01D 57/02
[52] U.S. Cl. .............................. 204/301; 204/300 R; 204/299 R; 204/180.1
[58] Field of Search ............ 204/299 R, 180.1, 300 R, 204/183.1, 183.2, 301, 182.3

[56] References Cited

U.S. PATENT DOCUMENTS

| | | | |
|---|---|---|---|
| 3,563,872 | 2/1971 | Huebner | 204/180.1 |
| 3,616,453 | 10/1971 | Philpot | 204/299 R |
| 3,758,395 | 9/1973 | Strickler | 204/183.1 X |
| 4,670,119 | 6/1987 | Hurd | 204/183.2 |
| 4,732,656 | 3/1988 | Hurd | 204/183.1 X |
| 4,900,421 | 2/1990 | Grutzner et al. | 204/299 R |

FOREIGN PATENT DOCUMENTS

0356187A2 8/1989 European Pat. Off. ...... G01N 27/26

OTHER PUBLICATIONS

Rotofor brochure entitled *A Revolutionary Device for High Resolution Preparative Electrophoresis* by Bio-Rad Laboratories Chemical Division (undated).
Article entitled *The Development of Recycle Zone Electrophoresis* by Cornelius F. Ivory, Department of Chemical Engineering, Washington State University, 1990.

*Primary Examiner*—John Niebling
*Assistant Examiner*—John S. Starsiak, Jr.
*Attorney, Agent, or Firm*—Wells, St. John, Roberts, Gregory & Matkin

[57] ABSTRACT

An electrophoretic processor for separating proteins and other chemicals exhibiting varying electrophoretic mobilities. The preferred processor includes a rotor which turns within a stator to define a processing chamber therebetween. The rotor and stator are preferably cylindrical to provide an cylindrically annular processing chamber which will induce transverse secondary flows, preferably in the form of toroidal vortices. The transverse toroidal vortices improve heat transfer and counteract longitudinal flows which decrease separation. Embodiments are described which include multizone electric fields. The resulting electric fields are varied in strength to focus mobile molecules against a countervailing flow of carrier fluid. The described processors can be used to perform a variety of processes including batch and continuous flow zone electrophoresis and batch isoelectric focusing.

38 Claims, 14 Drawing Sheets

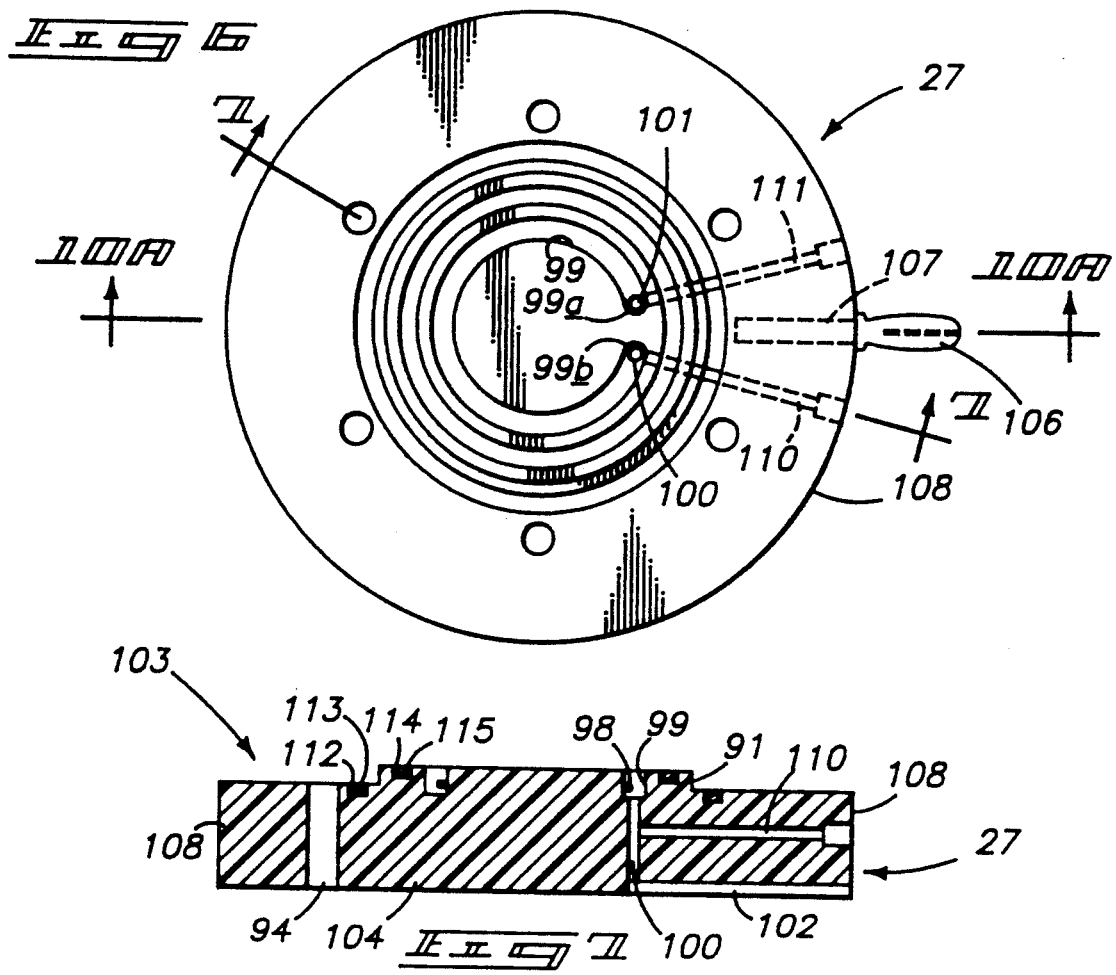
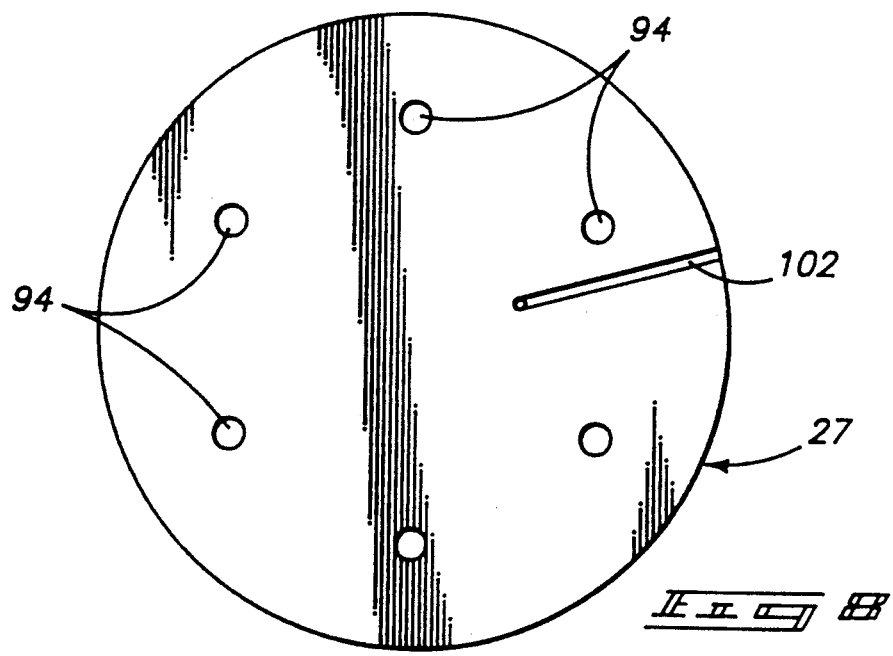

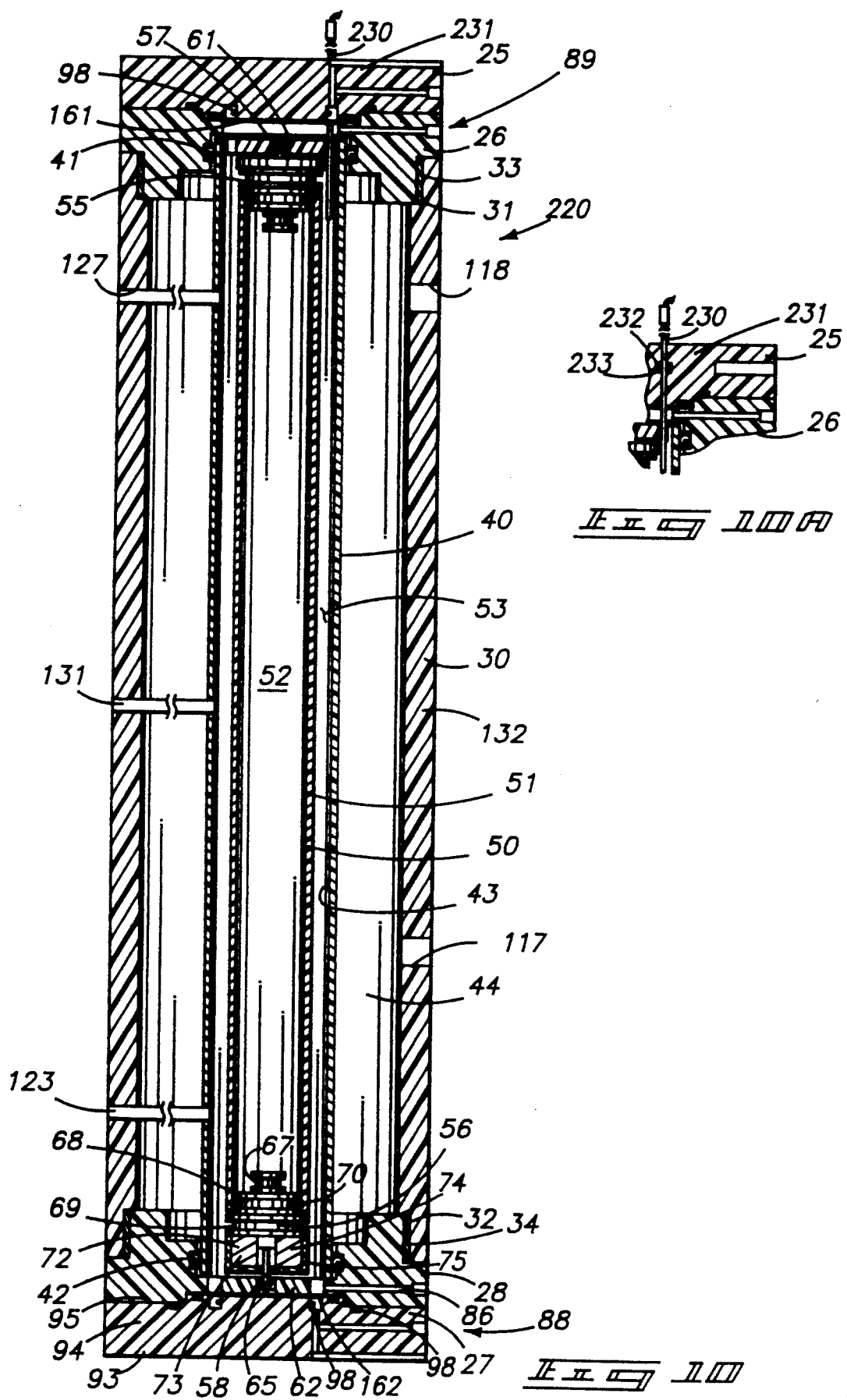

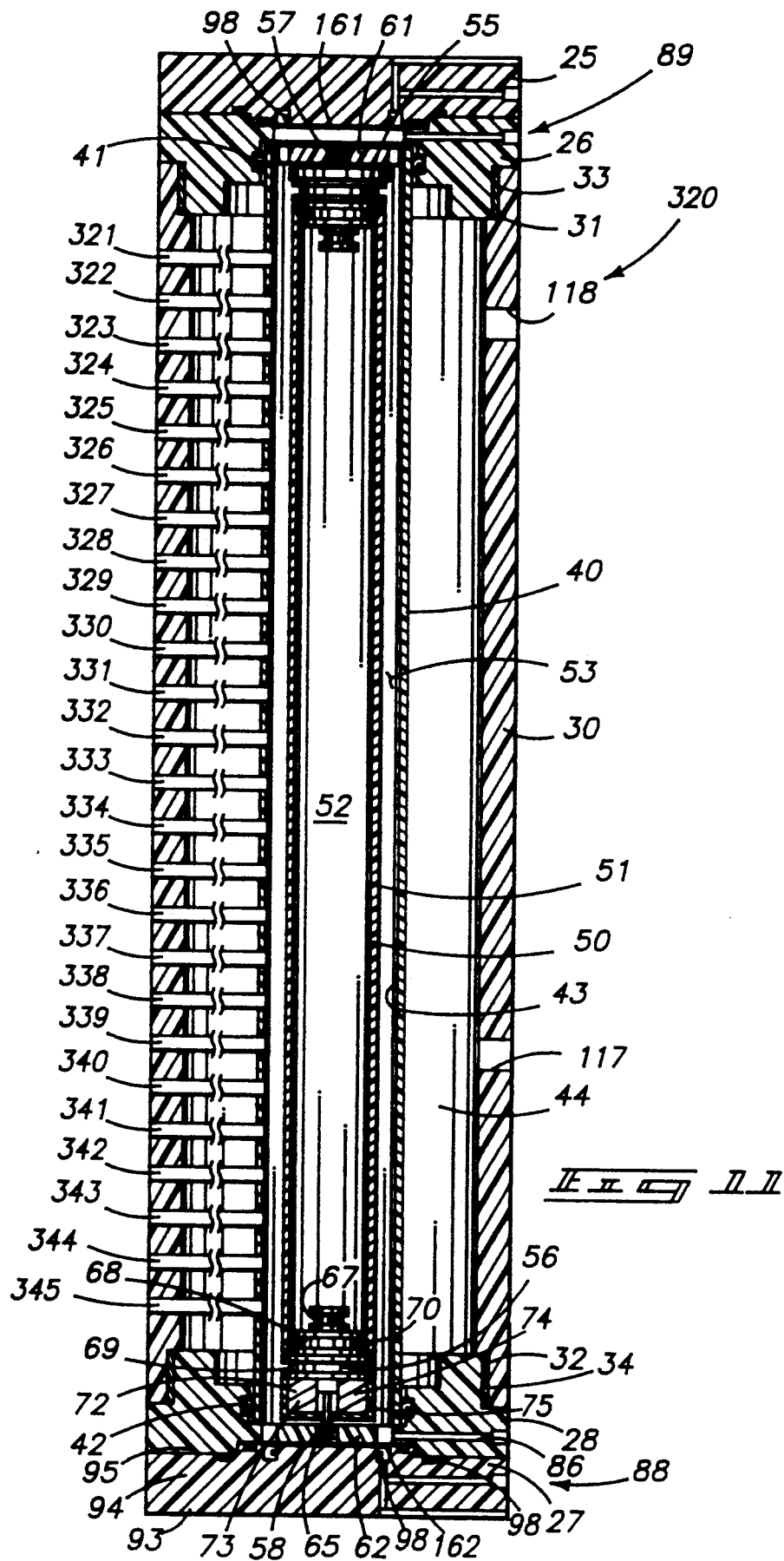

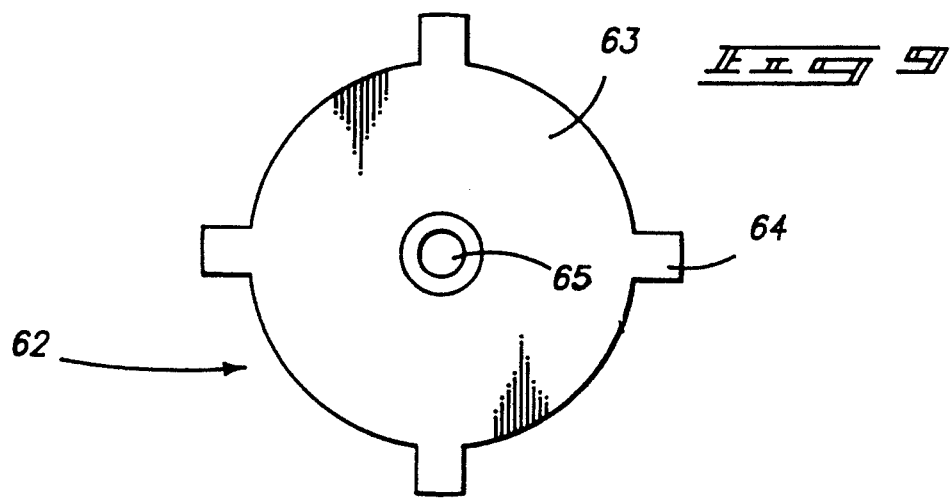
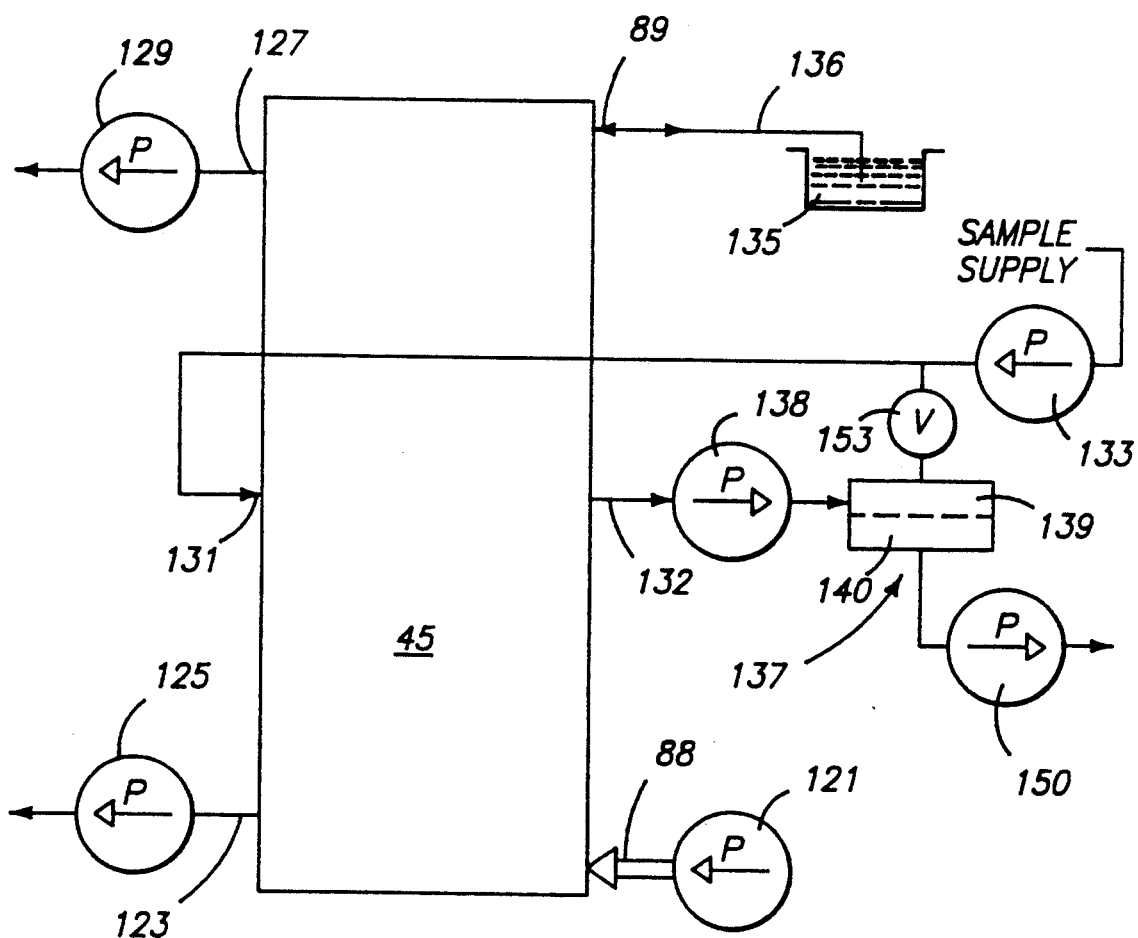

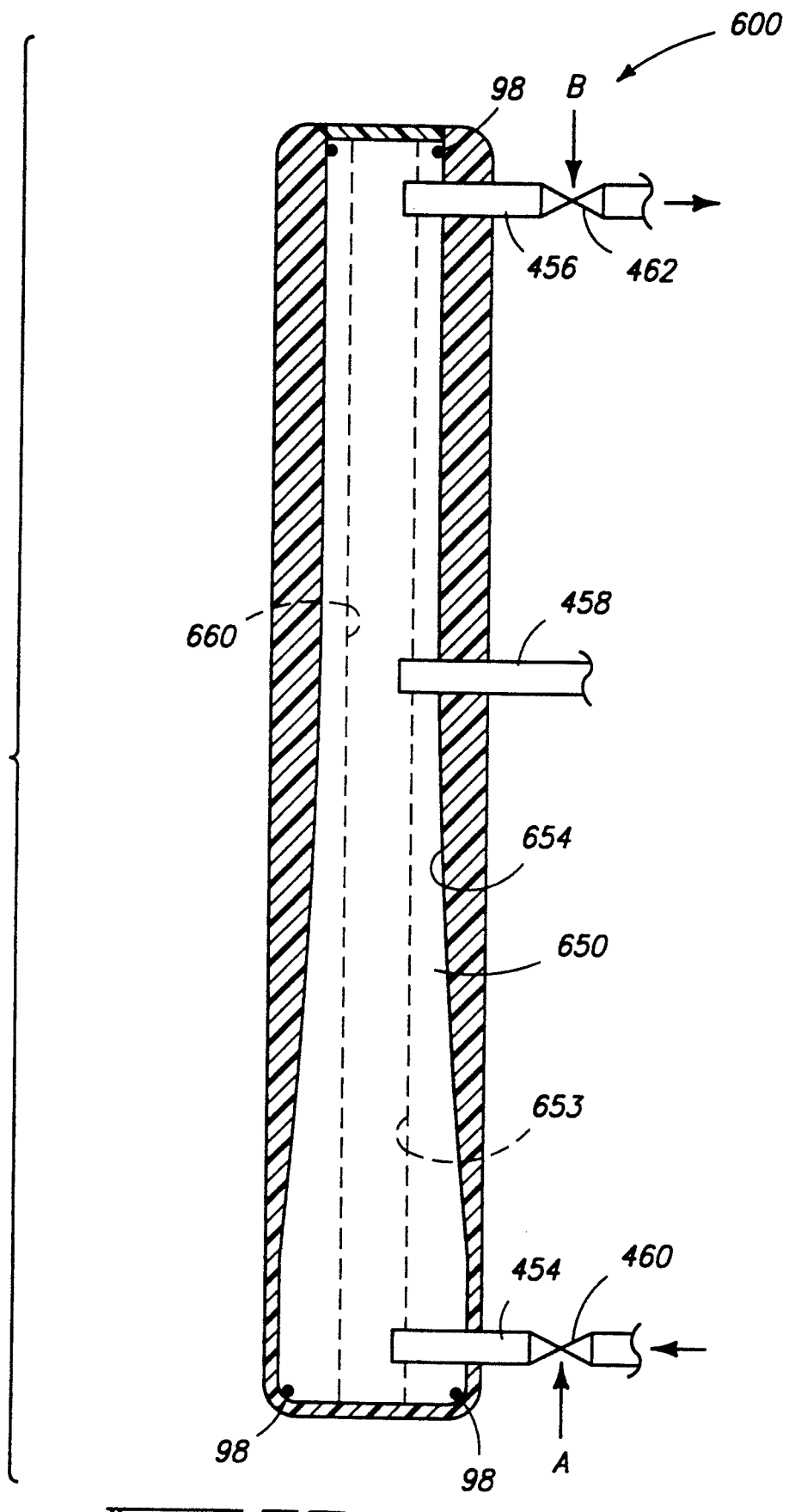

ELECTROPHORETIC PROCESSING

CROSS REFERENCE TO RELATED APPLICATIONS

This patent is a continuation-in-part application from copending U.S. patent application Ser. No. 07/782,692, filed Oct. 25, 1991 now U.S. Pat. No. 5,200,050.

TECHNICAL FIELD

The technical field of this invention is electrophoretic processors and related methods of electrophoretic processing, particularly electrophoretic separation of proteins.

BACKGROUND OF THE INVENTION

Over the last 20 years there have been great advancements in protein synthesis, recombinant organism expression of complex molecules, particularly proteins, and hybridization of cells to produce monoclonal antibodies. These and other developments have lead to increasing need for apparatus and methods for efficiently separating desired products from co-products and various other contaminants.

Electrophoresis has been previously used for protein and peptide separation. However, electrophoresis has in general been performed at low flow rates not adapted to preparative scale production to provide significant quantities of the desired products. Many prior art electrophoretic separation systems utilize a confined chamber formed between two plates. An electric field is established between two opposing electrodes or in a desired two-dimensional array using additional electrodes. Such systems typically have good resolution of proteins but have limited flow rates. They are also typically limited to a single type of processing. They are further relatively complex and costly and troublesome to operate at preparative scale sizes. Preparative scale systems must be contrasted to laboratory scale systems used to discriminate proteins contained in samples for identification and extraction in very limited quantities.

One preparative scale electrophoresis apparatus is the ROTOFOR ® by Bio-Rad Laboratories of Richmond, Calif. 94804. This apparatus performs preparative scale free solution isoelectric focusing of proteins using a rotating electrophoretic processing chamber. The rotating electrophoretic processing chamber has a horizontal axis of rotation which extends between the electrodes. The processing chamber is divided into twenty discrete compartments using membrane screens which are transversely placed along the horizontal axis. An ampholyte solution is used to create a pH gradient between the charged electrodes. The varying pH along the chamber allows proteins to selectively collect (focus) at the pH corresponding to their associated isoelectric points. Thus proteins having differing isoelectric points can in many cases be separated into one of the discrete compartments.

The ROTOFOR performs only in a batch mode of operation and only performs isoelectric focusing. The batch operation takes about 4 hours, thereby limiting the processing rates which can be achieved. This unit further must be stopped to extract the separated proteins and cannot be used in a continuous flow mode of operation. The separated fractions are removed using a harvesting apparatus having a series of tubes which tap the processing chamber at various fixed locations along the axis between the electrodes. This unit is also relatively costly to operate.

One apparatus of the current invention is advantageous in providing a construction having features which allow it to be used for several different types of electrokinetic separation. Electrophoresis can be performed in both batch and continuous flow modes of operation. Additionally, batch isoelectric focusing can be performed and extraction at various locations from the processing chamber can be accomplished. The system is relatively less complex than prior systems. It is also relatively low cost in both operation and initial construction of the system. It further provides improved heat transfer and resists problems due to electroosmosis while providing good separation of most proteins or other processed chemicals of varying electrophoretic mobilities.

Isoelectric electrophoresis processes use an ampholyte mixture to establish a pH gradient. Ampholytes and other buffer modifiers are expensive, thus increase processing costs. Another apparatus of this invention is advantageous in that electrophoretic processes can be carried out without use of expensive ampholyte buffers.

BRIEF DESCRIPTION OF THE DRAWINGS

One or more preferred forms of the invention are described herein with reference to the accompanying drawings. The drawings are briefly described below.

FIG. 6 is a top view of the bottom electrode holder forming part of the processor of FIG. 1 in isolation.

FIG. 7 is a sectional view of the bottom electrode holder of FIG. 6 taken along section line 7—7 thereof.

FIG. 8 is a bottom view of the bottom electrode holder shown in FIG. 6.

FIG. 9 is a top view of the rotor mount forming part of the processor of FIG. 1 in isolation.

FIG. 10 is a longitudinal sectional view similar to FIG. 2 showing an alternative embodiment.

FIG. 10A is an enlarged sectional view showing the catheter mounting portion forming a part of FIG. 10.

FIG. 11 is a longitudinal sectional view similar to FIG. 2 showing a further alternative embodiment.

FIG. 13 is a schematic view showing the processor of FIG. 1 connected in a processing system useful in performing methods as explained in greater detail herein.

FIG. 20 is a diagrammatic sectional view of an alternative electrophoretic processor of this invention.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

Electrophoretic Processors

Figure 1:
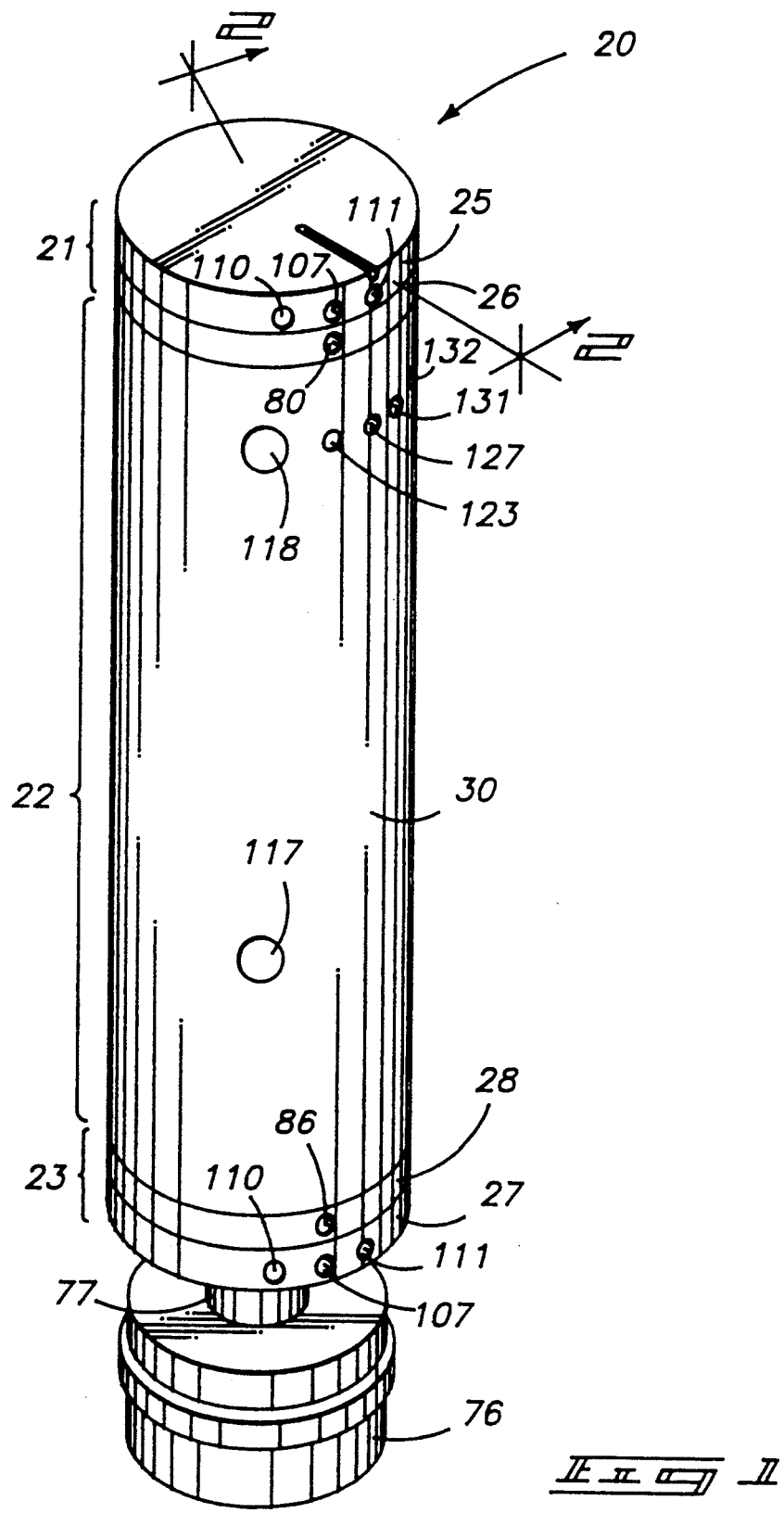
FIG. 1 is a perspective view showing a novel electrophoretic processor constructed according to the principles of this invention.

FIG. 1 shows a preferred electrophoretic processor 20 constructed according to this invention. Processor 20 includes a top end section 21, central section 22 and bottom end section 23. The top or first end section 21 includes a top or first electrode holder 25. It also includes a top or first end piece 26. The bottom or second end section 23 includes corresponding bottom or second electrode holder 27 and bottom or second end piece 28.

Figure 2:
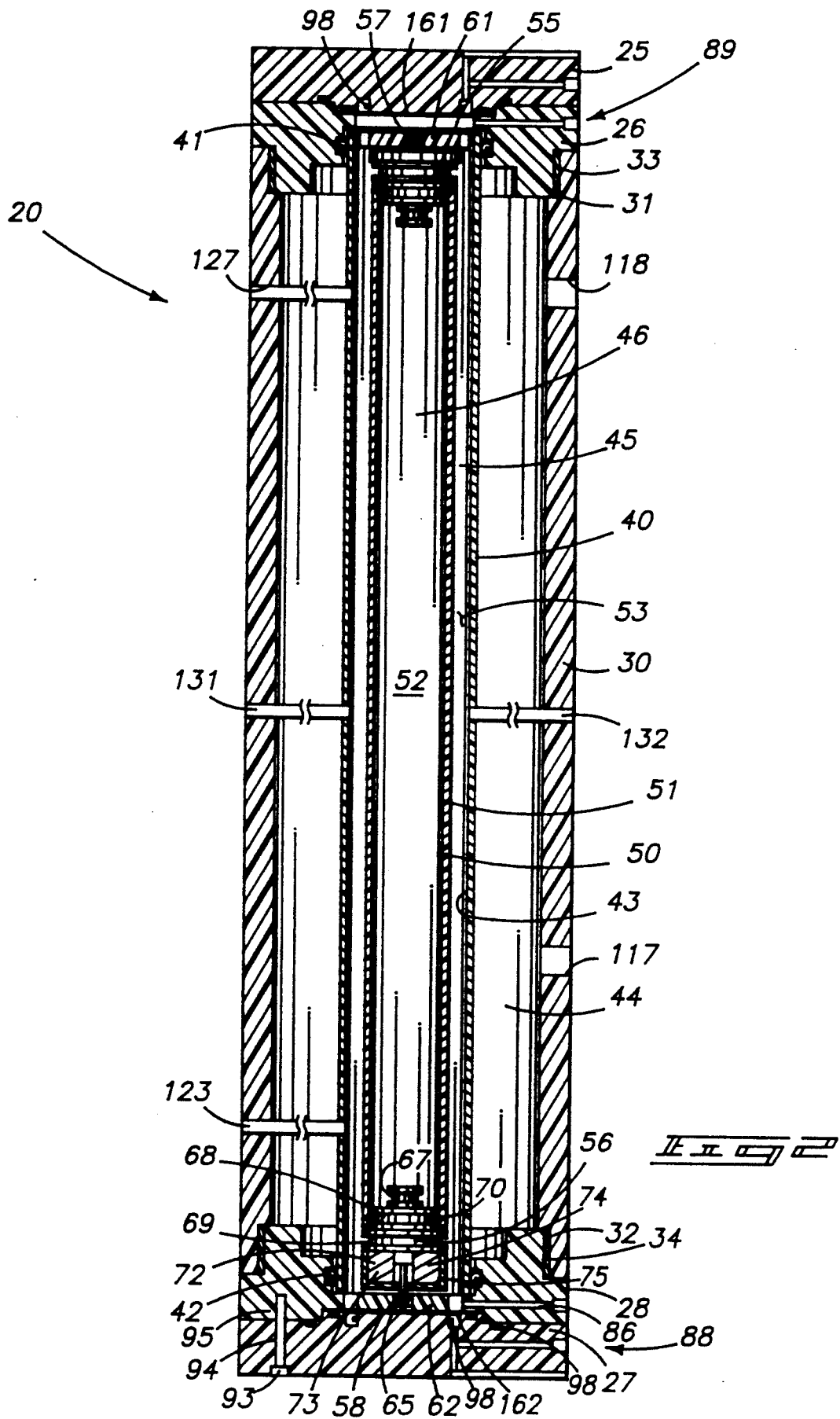
FIG. 2 is a longitudinal sectional view of principle parts of the processor of FIG. 1 taken along line 2—2 thereof.

Central section 22 includes an outer tube 30. Outer tube 30 is connected to the top and bottom end sections, specifically at end pieces 26 and 28. FIG. 2 shows this connection is advantageously provided using female threaded sections 31 and 32 formed at the upper and lower ends of outer tube 30 along the interior thereof. The female threaded sections 31 and 32 receive appropriately sized male threaded sections 33 and 34 formed on end pieces 26 and 28, respectively. The outer tube is and end sections are preferably made of PLEXIGLAS or other suitable transparent plastic material.

FIG. 2 also shows that the central section includes a stator 40 and rotor 50. Stator 40 is advantageously a tubular member having approximately cylindrical interior surfaces 43. Stator 40 is most preferably a cylindrical tube made of glass. The stator is held in a stationary position by interior bores formed within top and bottom end pieces 26 and 28. Top and bottom O-ring seals 41 and 42 are advantageously used to seal between the outer surfaces of the stator and the adjacent interior bore of the end pieces.

The outer surfaces of the stator serve to partially define a temperature stabilization chamber 44 which is formed within the outer tube 30 outside of stator 40. Outer tube 30 is preferably provided with heat transfer media communication ports 117 and 118 through which chilled water or other suitable heat transfer or cooling media can be communicated into chamber 44. Typically the temperature stabilization chamber 44 will be provided with a cooling media to remove heat dissipated within the processing chamber 45 due to Joule heating of the working fluid as current is passed therethrough between the electrodes 98. Other alternative temperature stabilization or control techniques can be utilized as is needed or appropriate.

Rotor 50 most preferably includes a tubular cylinder 52 which is held by two rotor end pieces 55 and 56 connected to the rotor tube at opposing ends thereof. The rotor tube is preferably made of glass. The rotor end pieces are preferably made of plastic, such as the preferred PLEXIGLAS.

Rotor 50 is preferably formed with approximately cylindrical exterior surfaces 51 which are juxtaposed to the interior surfaces 43 of the stator. In the preferred embodiment, the cylindrical interior surfaces of the stator and the cylindrical exterior surfaces of the rotor are spaced to provide an annular space which serves as a processing chamber 45. The radial distance between the rotor and stator is radial gap 53. The radial gap 53 is preferably approximately uniform about the rotor, although substantial variation (+ −50%) can occur while still providing operability in at least some apparatuses according to this invention. The preferred cylindrical rotor configuration defines a rotor cylinder axis which preferably coincides with the rotational axis of the rotor end pieces 55 and 56.

The rotor is preferably mounted for rotation within the stator by the rotor end pieces. FIG. 2 shows that rotor end pieces 55 and 56 are provided with pin-like rotation shafts 57 and 58, respectively, which are received within rotor mounting pieces 61 and 62. Shafts 57 and 58 are preferably made of stainless steel or other suitable material.

FIG. 9 shows the bottom rotor mount 62 in greater detail. Rotor mount 61 is the same or substantially the same. The rotor mounts include a main part 63 which is provided with a generally circular peripheral shape. Extending from the periphery of the rotor mount main pieces 63 are a plurality of locating extensions 64. The locating extensions 64 are sized to fit within the interior of the stator, thereby radially positioning the rotor mounts therewithin. The rotor mounting pieces 61 and 62 are provided with pivot bearing inserts 65. The pin shafts 57 and 58 extending from the upper and lower rotor end pieces are received within receptacles formed in the pivot bearing inserts 65. The pivot bearing inserts are advantageously formed of stainless steel or other suitable wear and corrosion-resistant material. Remaining portions of the rotor mounts can be made of a variety of suitable plastic materials, such as the preferred PLEXIGLAS.

The rotor end pieces 55 and 56 are preferably provided with three differently sized seal grooves 67, 68 and 69. The minor diameter grooves 67 are sized to receive a small O-ring which seals with the interior diameter of a small rotor (not shown). The medium diameter grooves 68 are sized to receive O-rings 70 which seal to the interior surfaces of rotor 50. Major diameter grooves 69 are larger in diameter than grooves 67 and 68 and are sized to receive O-rings (not shown) which seal to the interior surfaces of an alternative rotor (not shown). This construction for end pieces 55 and 56 allows three different rotor sizes to be accommodated to vary the radial gap between the rotor exterior surfaces and the stator interior surfaces.

Exemplary sizes of rotors in one preferred embodiment of the invention include rotor tube sizes of 1, 1.9, and 2.2 centimeters diameter for the three different sizes. The stator inside diameter is 2.5 centimeters. The associated radial gaps between the rotor exterior surfaces and the interior surfaces of the stator are 0.75, 0.3, and 0.15 centimeter, respectively. All three rotors have similar overall lengths of approximately 25 centimeters. The outer diameter of the outer tube 30 is advantageously approximately 7 centimeters. Other sizes for the rotor, stator and outer tube are alternatively possible.

Bottom rotor end piece 56 is further advantageously adapted to allow the rotor to be driven. In the preferred embodiments shown herein, the bottom end piece is connected to a magnet assembly 72 which has a north pole 73 and south pole 74. Magnet assembly 72 preferably is encapsulated within a protective capsule 75 to prevent corrosion and electrical short circuiting. The capsule 75 can advantageously be made of silicone rubber or other suitable material. FIG. 1 shows a rotor drive in the form of an electric motor 76 and drive magnet 77 which is connected to turn with rotation of the shaft of motor 76. Rotation of drive magnet 77 causes a rotating magnetic field which applies torque to rotor magnet 72 causing rotation thereof in the same direction to form a magnetic coupling. The motor 76 and magnetic drive 77 have been omitted from Figures other than FIG. 1 for sake of convenience.

Processing chamber 53 between the stator and rotor is preferably provided with fluid communication ports for inflow and outflow of fluids. This is advantageously done using ports 123, 127, 131 and 132 which extend through the stator. Ports 86 and 89 extend through the end pieces to provide fluid communication at the ends of the processing chamber. In FIG. 2 the stator penetrating ports are shown for convenience as extending directly through the outer tube 30. However, it is also possible to run the connecting conduits in more lengthy arrangements within chamber 44 and have the ports open at various points, such as together in an array as illustrated solely in FIG. 1. Many alternative arrangements are possible.

Figure 3:
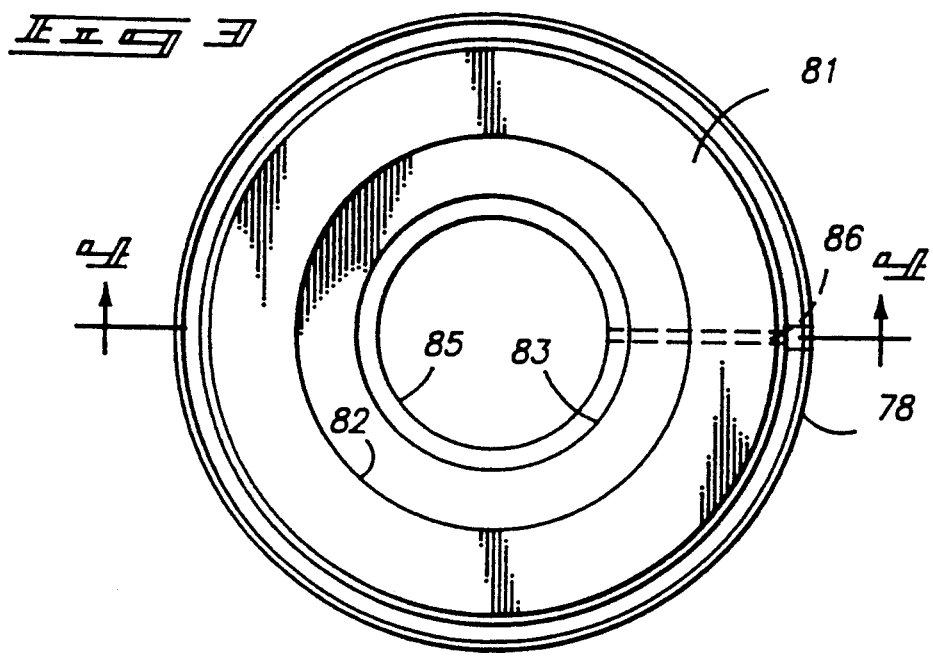
FIG. 3 is a top view of the bottom end piece forming part of the processor of FIG. 1 in isolation.
Figure 4:
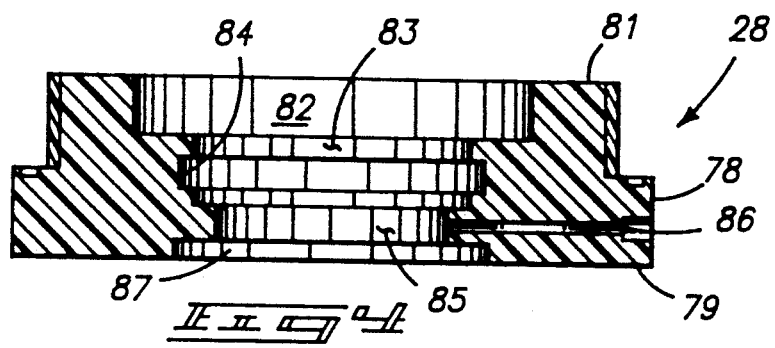
FIG. 4 is a side sectional view of the bottom end piece shown in FIG. 3 taken along line 4—4 thereof.
Figure 5:
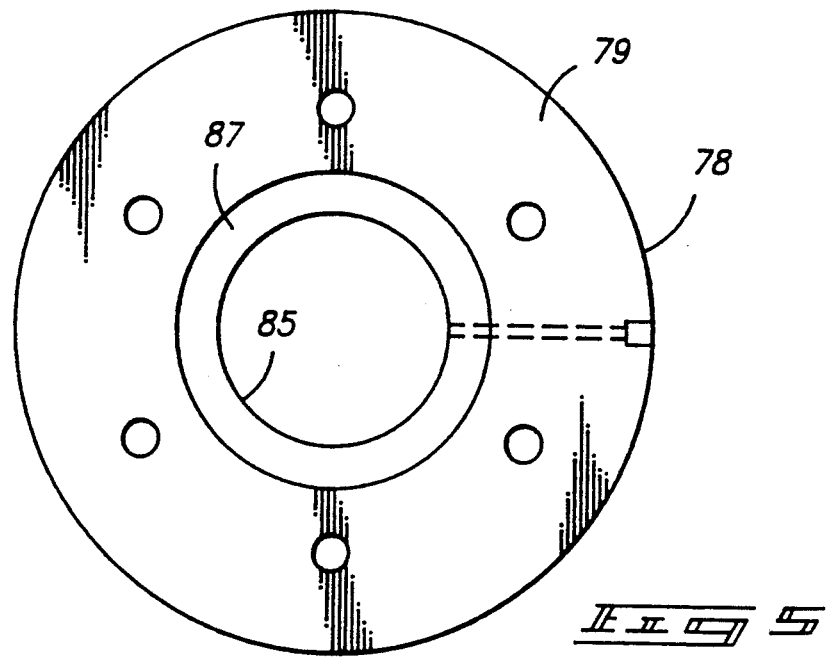
FIG. 5 is a bottom view of the bottom end piece shown in FIG. 3.

FIGS. 3-5 shows the bottom end piece 28 is greater detail. The top end piece is constructed similarly. The top and bottom end pieces 26 and 28 have exterior sidewalls 78 which extend between the distal face 79 and the flange face 80. Flange face 80 is adjacent to the threaded sections 32 and 33 explained hereinabove. Pieces 26 and 28 also include a proximal face 81 which faces inwardly toward the processing chamber. The central portions of pieces 26 and 28 include large bores 82. Adjacent to large bore 82 is a step which reduces the diameter of medium bore 83 to a size sufficient to receive the stator 40 in close proximity thereto. O-ring 42 (FIG. 2) is received within an O-ring seal groove 84 along the interior diameter of the medium bore 83. The small bore 85 of pieces 26 and 28 is approximately the same inner diameter as the inner diameter of stator 40. This provides a relatively constant inner diameter against which the rotor mount pieces 61 and 62 can fit adjacent either the small bore 85 or interior surfaces 43 of the stator.

The first and second end pieces 26 and 28 are also provided with at least one fluid passageway 86. As shown, passageway 86 extends from the outer sidewall 78 inwardly to open along the interior surface of the small bore 85. The fluid passageway 86 formed in bottom end piece 28 forms a first or bottom processing fluid access port 88. Fluid passageway 86 formed in part 26 forms a second processing fluid access port 89.

The distal faces 79 of parts 26 and 28 are advantageously provided with a membrane receptacle 87 which receive upper and lower membranes 161 and 162. Face extensions 91 (see FIG. 7) formed on the faces of the electrode holding pieces 25 and 27 extend into the membrane receptacles on the opposing sides of the membranes to provide support thereto. The membranes used in processor 20 can be of several different types. They are intended to isolate electrolyte which surrounds the electrodes 98 held in grooves 99, from the working fluid held in the processing chamber and related ports and passageways. The electrolyte facilitates the flow of current to the working fluid contained in the processing chamber. Dialysis membranes well known in the art are used when the processor is operated for zone electrophoresis separations. When the processor is used for isoelectric focusing methods, then the membrane adjacent the anode is any suitable cation-exchange membrane, and the membrane adjacent the cathode is any suitable anion-exchange membrane, both well known in the art.

FIGS. 6-8 show electrode holders 25 and 27 in greater detail. Electrode holders 25 and 27 are held in position using suitable fastening means, such as the array of six or other appropriate number of fasteners 93 which extend through fastener holds 94 and into appropriately formed receptacles 95 formed in end pieces 26 and 28. As shown, the fasteners are arranged in a regular hexagonal array about the longitudinal axis of processor 20. Fasteners 93 are preferably made from a non-ferrous and non-magnetic material, such as aluminum or magnesium, to minimize any effects on the magnetic rotor drive.

The interior faces of the electrode holders are provided with the central extensions 91 which serve to support electrode membranes 161 and 162 (see FIG. 2). An electrode 98 is received within electrode groove 99. The electrode groove 99 is semi-circular, running from a first terminus 99a to a second terminus 99b. The termini 99a and 99b are in fluid communication with axial electrolyte passages 100 and 101. Axial electrode passage 100 extends to an electrode lead groove 102 formed in the exterior face 104 of electrode holders 25 and 27. Groove 102 allows an electrode lead wire to be extended from electrode 98 outwardly and through groove 102 and across the outer sidewall 108 for connection with an electrode connection plug 106 (shown only in FIG. 6). Groove 102 is sealed with a suitable sealant such as silicon rubber after passing the electrode lead wire therethrough. This keeps fluids from passing out of passage 100. Electrode connection plug 106 is mounted within an aperture 107 formed in the sidewall 108.

The electrodes are connected to a suitable electrical power supply (not shown) which is capable of charging the electrodes to the desired voltages and providing sufficient current through the processing chamber. A variety of power supplies now used in electrophoretic systems can be used. The typical voltage ranges are 1000-2000 volts across the electrodes. This establishes and electrical field having a field gradient which extends over a distance of approximately 25 centimeters in the preferred embodiment described herein. The current requirements of the power supply will vary dependent upon the processing fluid. Typically power supplies capable of delivering variable or constant current outputs up to approximate 1 amp at the indicated voltages will be appropriate for use in this invention.

The axial electrolyte passageway 100 also connects with a first electrolyte radial passage 110. Similarly, axial passageway 101 connects with a second radial electrolyte passage 111. In preferred operating modes, electrolyte can be circulated through the electrolyte groove 99 by forcing it in and out through passageways 110, 100, 99, 101 and 111 in either direction.

When processor 20 is used in zone electrophoresis modes of operation, than the electrode electrolyte can be a range of suitable fluids, most easily the buffer solution typically used as the working fluid. In the isoelectric focusing mode of operation, the anode electrolyte should be a relatively strong acid solution, e.g. 0.1M phosphoric acid, and the cathode electrolyte should be a relatively strong basic solution, e.g. 0.1M sodium hydroxide. Many other alternative electrolytes can be used.

The outer ends of radial electrolyte flow passageways 110 and 111 form electrolyte ports which are advantageously provided with fittings (not shown). Tubing is connected to the fittings for conveying the electrolyte from a suitable source and to a suitable disposal or recycle system (not shown) as desired in the particular processing system.

The interior faces 103 of electrode holders 25 or 27 are each advantageously provided with an O-ring groove 112 which receives an O-ring 113. The inner portion of interior face 103 associated with extension 91 is similarly provided with an O-ring groove 114 and associated sealing O-ring 115. O-rings 113 seal against the outward or distal faces of the end pieces 26 and 28. O-rings 115 seal against the electrode membranes 161 and 162.

FIGS. 10 and 10A show an alternative electrophoretic processor 220 according to this invention. Processor 220 is similar to processor 20 described elsewhere herein. Parts similar to both processors 20 and 220 are referenced using the same reference numerals to simplify the description. Processor 220 differs from processor 20 only with respect to the features described below.

Processor 220 additionally includes a movable catheter 230 which is slidably received within a catheter aperture 231 formed through the top electrode holder 25. Catheter aperture 231 is positioned to allow the catheter 230 to be extended between extensions 64 on the top rotor mount 61. The catheter aperture is also aligned parallel to the longitudinal axis of the annular processing chamber 45 and at a radial position appropriate to allow extension along a line just inwardly from the interior surface 43 of stator 40. This construction allows extension of the distal end of the catheter into the processing chamber to varying depths to permit extraction of desired isoelectrically focused components of the fluid being processed.

The catheter aperture is preferably provided with an appropriate seal for slidably sealing about the catheter and between the electrode holder. As shown the catheter seal is provided in the form of an O-ring 232 held within an O-ring groove 233. The catheter is advantageously a metal tube of small diameter and high strength to allow repeated insertion and removal. For purposes of illustration catheter 230 is shown condensed in length; however, it is desirably of sufficient length to allow removal of any fraction contained within the processing chamber.

FIG. 11 shows a further alternative embodiment electrophoretic processor 320 according to this invention. Processor 320 is similar to processor 20 described elsewhere herein. Parts similar to both processors 20 and 320 are referenced using the same reference numerals to simplify the description given herein. Processor 320 differs from processor 20 only with respect to the features described below.

The stator 40 in processor 320 is provided with an array of spaced product ports 321-345. Ports 321-345 are advantageously provided with associated conduits which connect the ports through the outer tube 30 to allow extraction of the fractions developed during isoelectric focusing electrophoresis, as explained more fully hereinafter.

Figure 16:
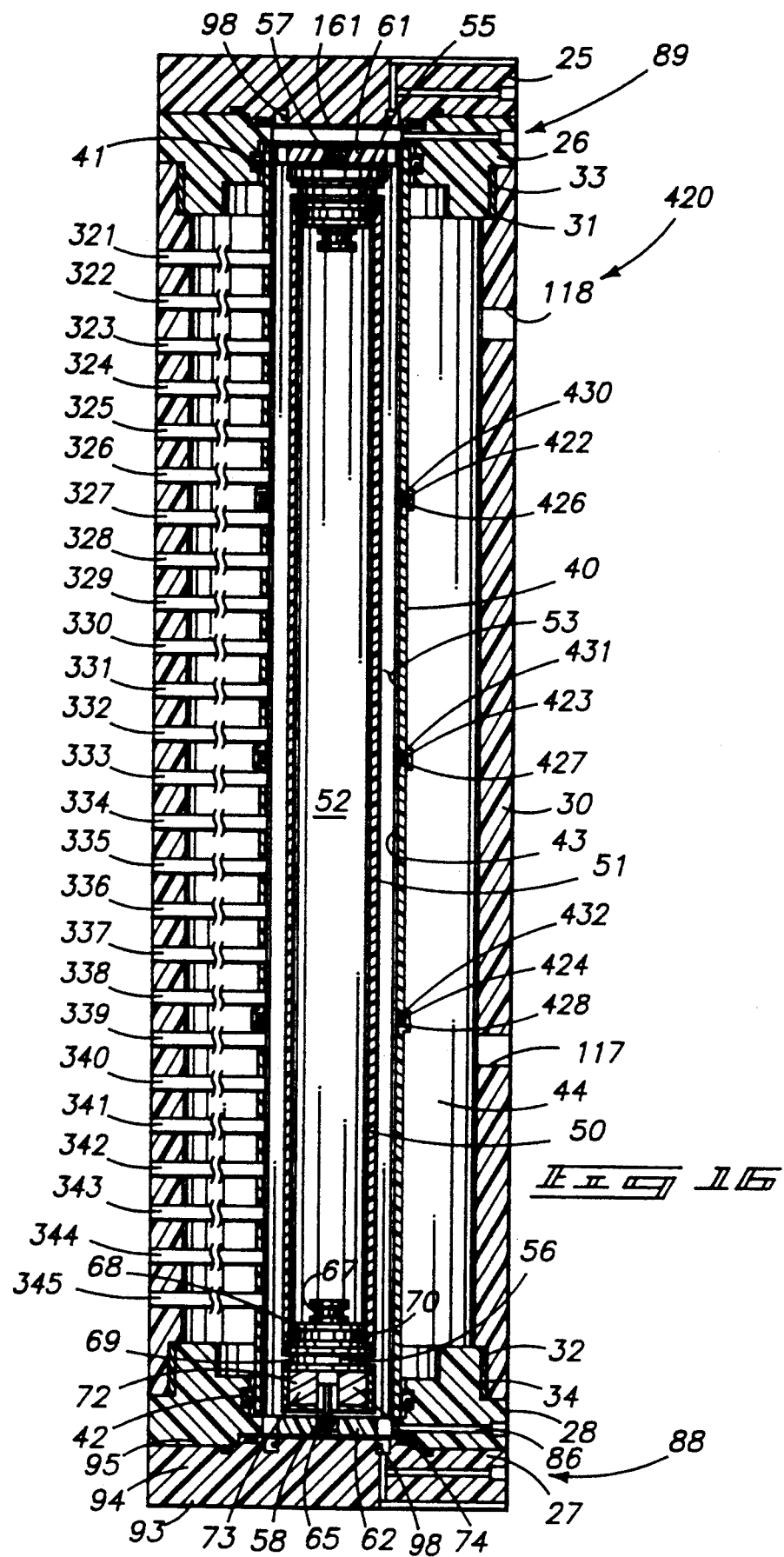
FIG. 16 is a longitudinal sectional view similar to FIG. 11 showing yet another alternative embodiment.
Figure 17:
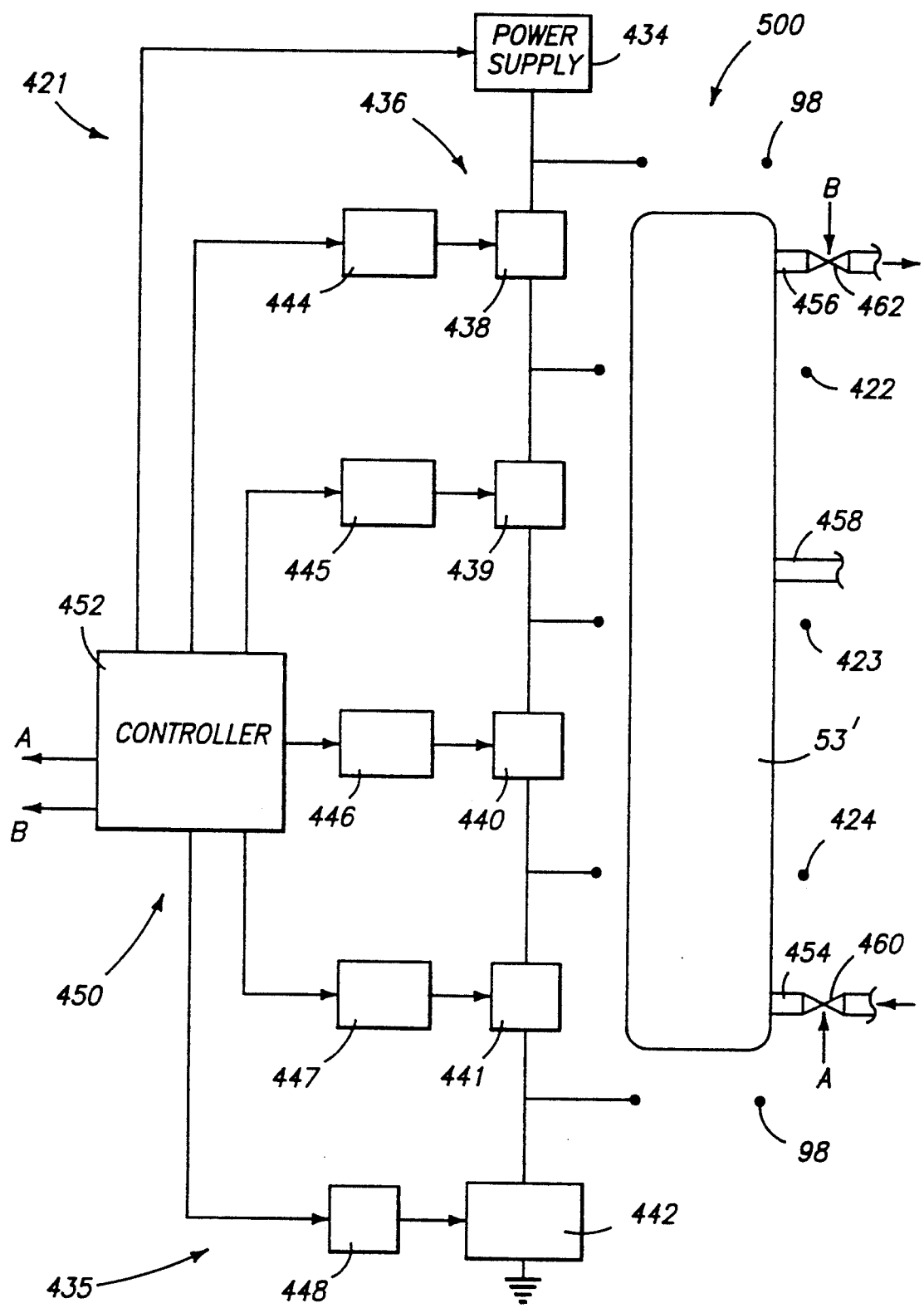
FIG. 17 is a diagrammatic schematic of the FIG. 16 processor embodiment and a control system for operating same.

FIGS. 16 and 17 show yet another alternative embodiment of an electrophoretic processor 420 according to this invention. Processor 420 is similar to processor 320 described above with respect to FIG. 11. Parts similar to processors 20, 320, and 420 are referenced using the same reference numerals to simplify the description given herein. Processor 420 differs from processor 320 only with respect to the features described below.

Processor 420 has a multi-zone electric field generator 421 for creating multiple processing zones having different field strengths within processing chamber 53. Multi-zone electric field generator 421 includes top and bottom electrodes 98 and plural intermediate electrodes 422-424 spaced longitudinally in a uniformly spaced longitudinal array as shown, or non-uniformly along processing chamber 53. Intermediate electrodes 422-424 are preferably annular, although other electrode configurations, such as discrete electrode points, can also be used. The annular or ring electrodes shown are preferably positioned within recesses or notches 426-428 formed in the interior surface 43 of stator 40. The intermediate electrodes are preferably arranged within planes transverse to the longitudinal axis of the processing chamber. Most preferably the transverse planes of the angular electrodes are perpendicular to the longitudinal axis of processor 420. Electrode separation membranes, such as dialysis membranes 430-432 overlie the recess openings to cover associated electrodes 422-424 and isolate them from the processing chamber to prevent contact with electrophoretically mobile chemicals contained in chamber 53.

When the desired voltages are applied to the electrodes, multiple zones having different electric field strengths are produced. Changes in field strength occur at or near the intermediate electrodes 422-424 such that the electrodes define boundaries between adjacent electric field zones. More or less than three intermediate electrodes can be employed to produce a multi-zone electrical field profile. This profile of electric field strengths has associated changes in or the electric field or electric field gradients. The voltages and produced electric fields and the gradients or relationship or change between the electric fields can very with the desired processing task. For example, if the goal is to separate a target product from many contaiminating proteins having similar mobilities, more electrodes would prove helpful to create more electric fields with smaller differences in electric field strengths between the various zones.

The multi-zone electric field generator 421 applies desired electric potentials to the end electrodes 98 and intermediate electrodes 422-424 to achieve the desired electric field strength profile along the processing chamber. As shown in FIG. 17, multi-zone electric field generator 421 also includes a power supply 434 and a variable field control system 435. Field control system 435 permits adjustment of the voltages at the electrodes and accordingly the various field strengths within the processing zones which exist approximately between pairs of adjacent electrodes 98 and 422-424. As shown, variable field control system 435 consists of a controllable voltage divider 436 coupled to the electrodes and a resistance control system 450. The voltage divider and resistance control system provide multiple electrode voltage supply outputs coupled to the electrodes to define the voltages thereat and provide current sufficient to maintain the desired voltages.

Voltage divider 436 comprises multiple, serially connected resistive elements 438-442, with one resistive element being provided between pairs of adjacent electrodes. The voltage divider allows controllable monotonically varying voltage levels across each resistive element so that different electrical potentials can be applied to electrodes 98 and 422-424. In this manner, multi-zone electric field generator 421 establishes multiple electric field zones having different field strengths. Resistive elements 438-442 are preferably adjustable potentiometers with a broad range of resistances to facilitate a wide spectrum of selectable electric field strengths between pairs of neighboring electrodes.

Resistance control system 450 is provided to monitor and change the resistances of the resistive elements 438-442 in voltage divider 436 and preferably consists of drivers 444-448 and a controller 452 coupled to manage the drivers. Drivers 444-448 (such as servomechanical or stepper motors) are connected to controllably adjust the resistances of respective potentiometers 438-442 in response to instructions from controller 452. Controller 452 can be a microcontroller, microprocessor, or a personal computer which are preprogrammed to establish the desired field strength profile, or alternatively, are user-interactive to allow a user to define, establish, and modify the electric field processing zones created in chamber 53' during operation.

Although a fully user-interactive control system is described in this embodiment, simpler multi-zone electric field generators can be used in accordance with this invention. For example, the multi-zone electric field generator could comprise multiple electrodes and a fixed resistor voltage divider that applies preset voltages to associated electrodes. This simpler generator would be advantageous for routine, well-established separation or concentration processes where the focusing parameters of flow rate and electric field strengths are already well known. Alternatively, independent voltage supplies could be connected and controlled for each electrode to allow complete variability in the electric field profile. In yet another alternative, the generator could be configured to apply time-pulsed voltages to the electrodes. The power supply could be coupled to the electrodes through an electronic or mechanical switch that alternately opens and closes the power link therebetween to control the effective voltage within the focusing zones. The switch would couple the power to various pairs of electrodes at different frequencies to effectuate zones of different field strengths.

Zone electric field generator 421 can also be employed with processors other than the rotating electrophoretic processing chamber disclosed herein. Accordingly, the schematic of FIG. 17 generally shows processor 500 having a processing chamber 53' which could include both an annular chamber defined between a rotor and stator as in above embodiments, and other processing chambers of different geometries. As illustrated, processing chamber 53' forms a conduit having an inflow port 454 and an outflow port 456 which permit fluid communication to and from the chamber. Such ports are representative of ports 88 and 89 of FIG. 16. The inflow and outflow ports are spaced axially apart such that a carrier fluid can be introduced into the chamber at one axial location, moved therethrough, and then extracted from the chamber at a different axial location. A counterflow of carrier fluid can therefore be established within the chamber as is discussed below in greater detail.

Valves 460 and 462 are provided in line with inflow and outflow ports 454 and 456, respectively. Controller 452 is operably connected via control signals A and B to open and close valves 460 and 462 to govern the flow rate and volume of carrier fluid introduced into the chamber. Alternatively, valves 460 and 462 can be manually controlled.

With reference to FIG. 16, ports 321-345 permit extraction of fluids that have focused, such as near intermediate electrodes 422-424 during zone electric field gradient focusing, as explained more fully hereinafter. More particularly, plural ports are provided between each pair of intermediate electrodes to facilitate sample or other fluid introduction or product extraction at various locations within each zone or along the processing chamber. Port 458 is shown in FIG. 17 near the middle of chamber 53' to represent diagrammatically one of the ports 321-345 of FIG. 16.

FIG. 20 schematically shows a still further processor 600 in accordance with this invention. Processor 600 is similar to the processor 500 shown in FIG. 17 and description of common elements is not repeated and the same reference numbers are used to indicate similar parts. Processor 600 differs from process 500 in that it is provided with an internal chamber 650 having a varying cross-sectional area defined within chamber interior walls 654. Positioned within the internal chamber is a porous conduit membrane 660. Preferably, membrane 660 has a uniform cross-sectional so that fluid velocity is uniform. Membrane 660 is preferably tubular, and more preferably cylindrically tubular, although other geometrics are possible. The interior of tubular membrane 660 defines the processing chamber 653 which isolates a working space within which separation occurs. Carrier fluid flows in through inlet port 454 into chamber 653 and exits through outlet port 456. A relatively constant fluid flow velocity exists within the preferred cylindrical tubular membrane 660. Membrane 660 can advantageously be a dialysis membrane, such as described hereinabove.

Processor 600 additionally includes end electrodes 98 which are outside the membrane 600. The converging walls 654 cause the current density of electrical current flowing between electrodes 98 to concentrate toward the converging upper end. This changes the electrical field strength and allows processing which balances thy hydrodynamic forces and electrophoretic forces to achieve improved processing, such as concentration of desired molecules which achieve polar condition in the buffer or electric fields used within the processing chamber. The processor of FIG. 20 allows a continuously and monotonically varying electric field gradient to be produced which varies from a higher field strength near the smaller diameter upper end toward the larger diameter lower end.

Figure 18:
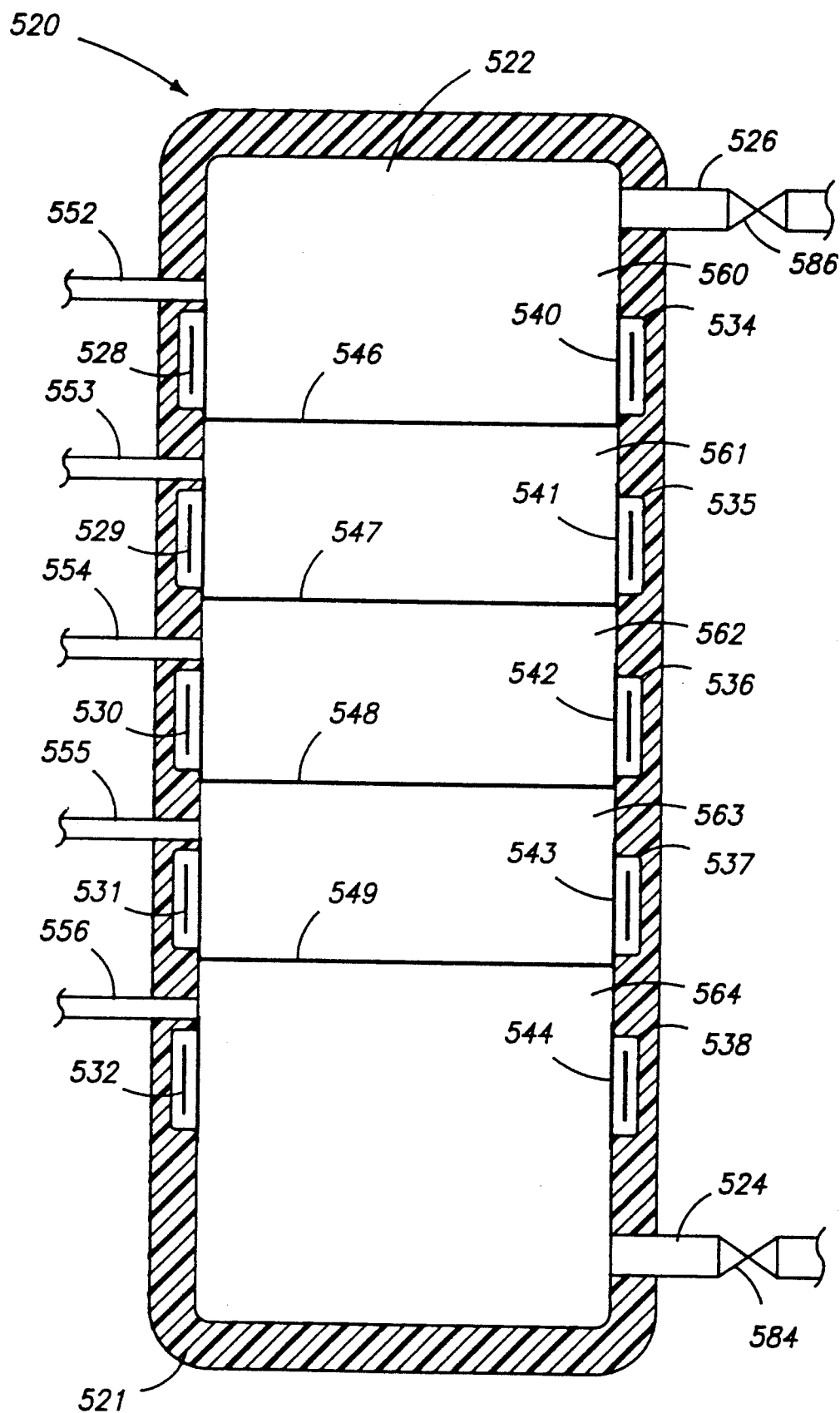
FIG. 18 is a diagrammatic longitudinal sectional view of an electrophoretic processor according to another aspect of this invention.

FIG. 18 shows another alternative embodiment of electrophoretic processor 520 according to this invention. Processor 520 includes a housing 521 which defines a processing chamber 522. Inflow port 524 and outflow port 526 provide fluid communication to and from chamber 522 and have controllable valves 584 and 586 provided in line to regulate the flow rate and volume into chamber 522. Such valves are preferably coupled to a controller, such as described above with respect to processor 420 in FIG. 17.

Processor 520 has multiple electrodes 528–532 which are preferably annular bands about processing chamber 522. The preferably annular electrodes are positioned within annular grooves or recesses 534–538 formed in the walls of housing 521. Thin annular dialysis membranes 540–544 cover the recess openings and isolate the electrodes 528–532 from the processing chamber 522.

Processing chamber 522 is divided into a series of processing compartments 560–564 by axially spaced electro-ultrafiltration membranes 546–549. Membranes 546–549 are preferably electro-ultrafiltration membranes, such as having a thickness and porosity that allows passage of both protein and buffer materials therethrough.

Different voltages are applied to respective electrodes 528–532 to establish electric fields of differing strength within processing chamber 522. Transverse compartment membranes 546–549 are positioned adjacent to corresponding electrodes 528–531 such that the membranes effectively define a boundary between two different electric fields. Relatively uniform field strengths are established within each chamber compartment, with relatively large electric fields being developed at or near the membranes. Processor 520 preferably includes a variable field control system coupled to electrodes 528–532 to permit user-controlled definition and modification of electric field strengths. However, a simpler voltage divider having plural serially connected fixed resistors which applies predetermined and set voltages to electrodes 528–532 can be employed.

Ports 552–556 provide fluid communication with chamber 522 to facilitate extraction from the multiple compartments 560–564. In this embodiment, one extraction port is provided form each compartment. However, plural extraction ports could be constructed for each compartment, similar to the design shown in FIG. 16.

Figure 19:
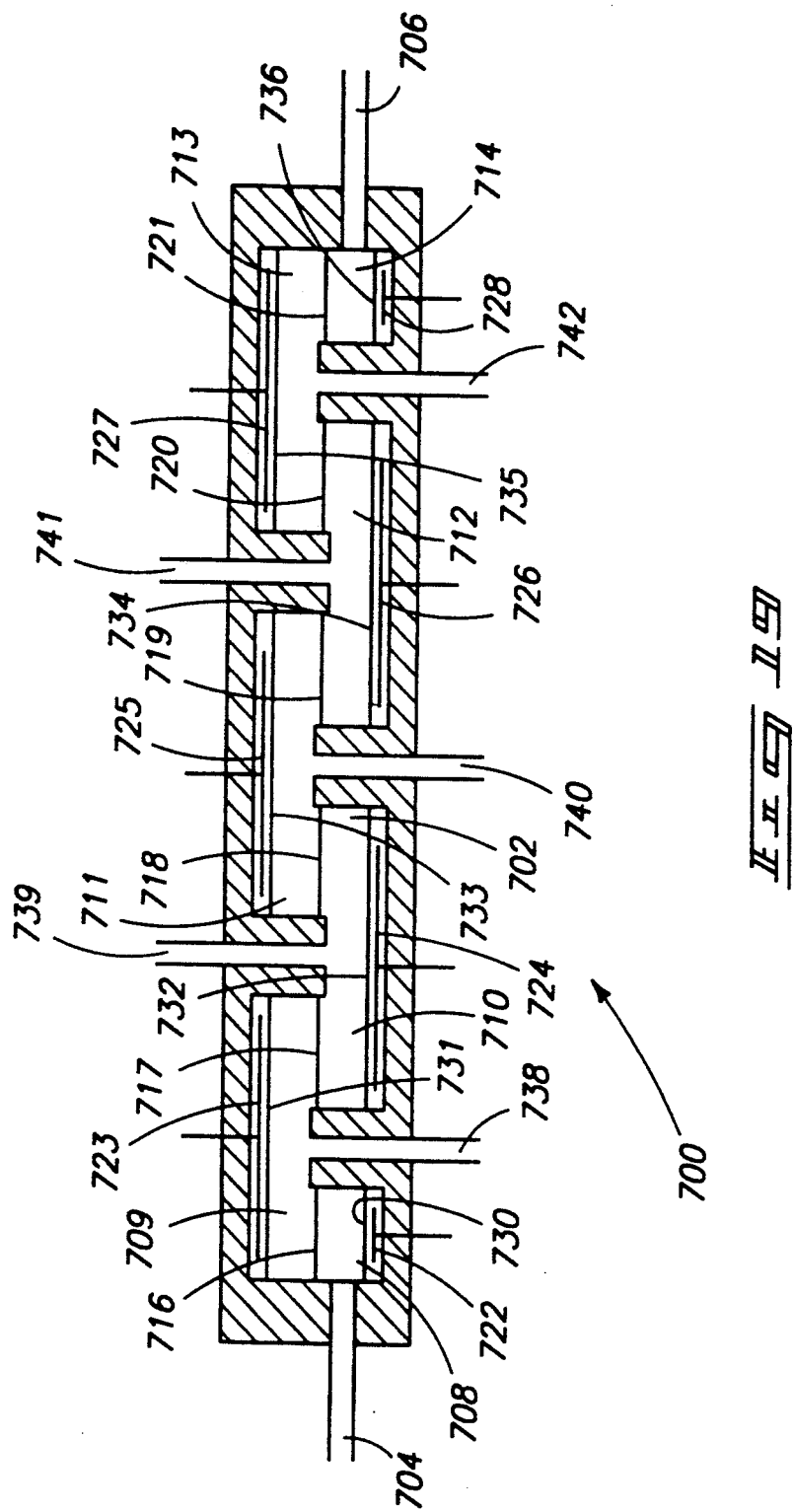
FIG. 19 is a diagrammatic longitudinal sectional view of an electrophoretic processor according to yet another aspect of this invention.

FIG. 19 shows a processor 700 which is similar in operation to processor 520, but is arranged in horizontal or planar fashion. Processor 700 has a processing chamber 702 with inflow and outflow ports 704 and 706. Chamber 702 is divided into compartments 708–714 via membrane 716–721 which are preferably dialysis membranes as above. Electrodes 722–728 are provided along the processor walls and are covered by dialysis membranes 730–736 to isolate the electrodes from chamber 702. Multiple extraction ports 738–742 provide fluid communication to associated compartments 709–713 of chamber 702.

SYSTEMS, OPERATION AND METHODS

The processors 20, 220, 320, 420, 500, 520, and 600 described herein can be operated in a number of different operational modes to effectuate novel processes according to this invention. The preferred operational modes include batch and continuous zone electrophoretic separation, isoelectric focusing separation, and zone electric field gradient focusing. In zone electrophoresis the electrophoretically mobile chemicals are processed in a working fluid having an approximately uniform pH. Molecules having different electrophoretic mobilities move through the working fluid at different rates dependent upon geometry, size, and the charge of the molecules. Isoelectric focusing and zone electric field gradient focusing are explained in greater detail below after explanation of the continuous and batch zone electrophoresis processing.

Figure 12:
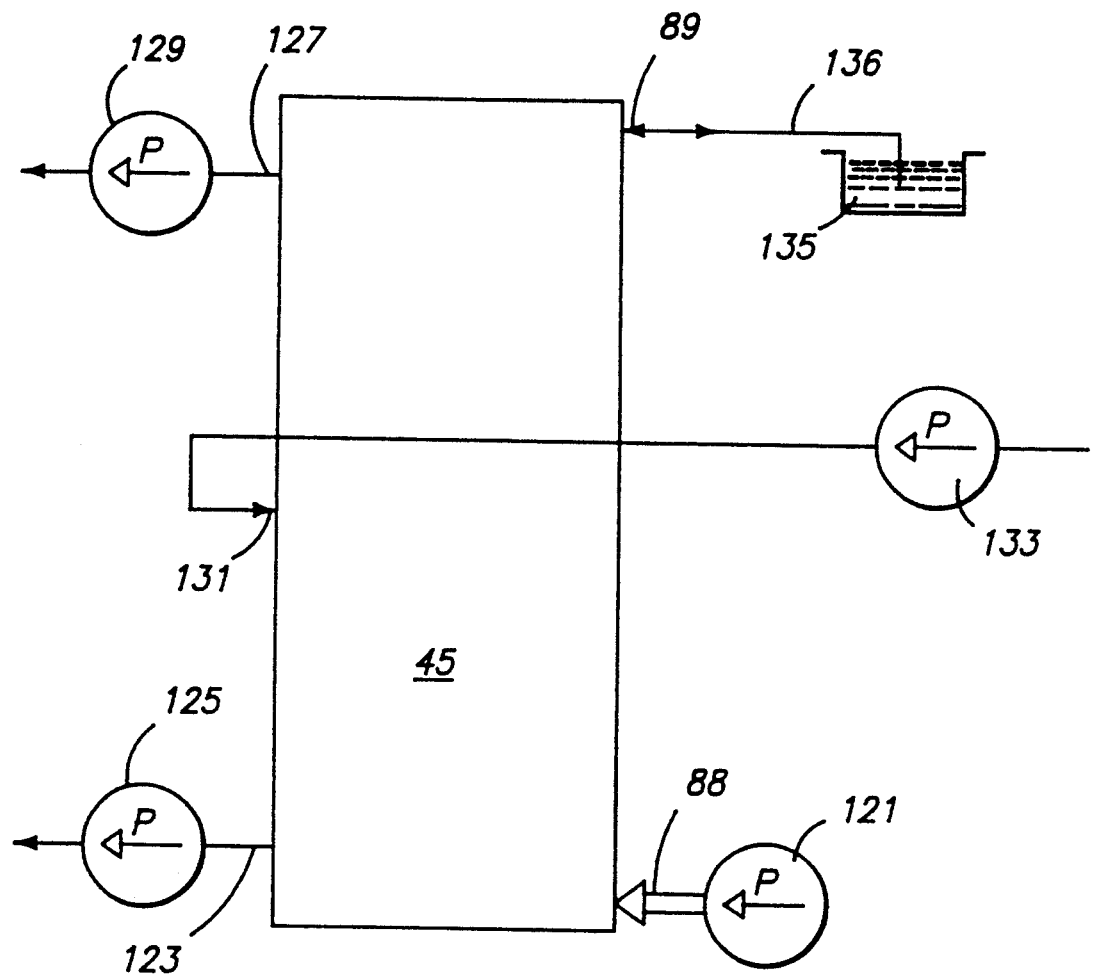
FIG. 12 is a schematic view showing the processor of FIG. 1 connected in a processing system useful in performing methods as explained in greater detail herein.

FIG. 12 shows a schematic representation of the processing chamber 45 of processor 20. Processor 20 is connected to allow continuous flow zone electrophoretic separation of two or more chemical fractions having different electrophoretic mobilities. The processing is preferably accomplished in the liquid phase using a working fluid. Examples of suitable working fluids include fluids such as electrophoresis buffer solutions suitable for the chemical system being processed. Such electrophoresis buffer solutions are well known in the art of free fluid electrophoresis separation. The flow of working fluid in through port 88 causes a working fluid flow within the process chamber 45 which is in opposition to the direction of molecule migration under the force of the electric field. The polarity of the electrodes 98 depends upon whether the molecules being separated assume negative or positive charges during electrophoresis in the working fluid selected.

The primary working fluid inlet port to the processing chamber 45 is bottom end piece fluid access port 88. A working fluid is supplied to port 88, such as by using pump 121. Pump 121 is advantageously a peristaltic tubing pump. The working fluid from pump 121 passes through port 88 and into the bottom portion of the processing chamber. The primary countercurrent working fluid flow supplied through port 88 is greater in rate than the flow rates of other individual flows into or from processing chamber 45. This establishes the counter-mobility fluid flow within the processing chamber. In preferred operation the counter-mobility working fluid flow is longitudinal in general direction, from bottom to top of the annular processing chamber 45.

A higher mobility outlet port 123 is positioned near but above the lower end of the processing chamber. In the preferred processor 20 about 2.5 centimeters above the lower end of the processing chamber. Port 123 removes about one half of the primary working fluid flow supplied by pump 121. The outflow through port 123 is induced by higher mobility outflow pump 125. The outflow at port 123 causes a substantial velocity decrease in the upwardly flowing working fluid. The greater velocity below port 123 in the lower terminating section of the processing chamber tends to sweep even the most mobile charged molecules upwardly to the level of port 123. The slower velocity above port 123 allows the higher mobility molecules to transit downwardly due to greater electrokinetic force than the hydrodynamic drag of the working fluid. Pump 125 is advantageously a peristaltic tubing pump, and can most conveniently be operated on a common peristaltic pump drive shaft with pump 121 to best coordinate the primary inflow and higher mobility port outflow rates.

FIG. 12 also shows a lower mobility outlet port 127 which is near but removed from the upper end of the processing chamber. In the preferred processor 20 about 2.5 centimeters below the upper end of the processing chamber. Outflow through port 127 is controlled by a lower mobility outflow pump 129. Pump 129 is also preferably a peristaltic tubing pump driven on a common drive with pumps 121 and 125. The lower mobility outflow rate is most preferably about equal to the higher mobility outflow rate, both equal to approximately one-half of the primary inflow rate provided by pump 121. The flow of fluid above port 127 will typically be small thus providing little or no effective counterflow drag on the charged molecules. This allows even molecules of very low mobility to transit downwardly in the upper terminating section of the processing chamber.

The sample containing the electrophoretically mobile molecules is advantageously fed through the sample feed inlet port 131 using a sample supply pump 133 and associated feed stream conduit 132. Pump 133 can advantageously be a syringe-type pump, well known in the art, or other suitable pump type. The sample is typically fed with the mobile chemicals in solution with the working fluid or other appropriate solute.

The system of FIG. 12 also includes means for balancing the fluid flows to and from the processing chamber 45. This fluid flow balancing means is advantageously in the form of a reservoir 135 containing a supply of working fluid therein. A conduit 136 extends from the upper end processing fluid access port 89 and beneath the level of the working fluid contained in reservoir 135. This arrangement allows working fluid to either be taken in or expelled from the processing chamber through port 89 as the other fluid flows to and from the processing chamber may require on an instantaneously changeable basis.

The system of FIG. 12 can be used to continuously process a feed stream containing molecules of differing electrophoretic mobilities to separate the feed stream into two fractions based upon mobility. The process includes feeding the feed stream into an approximately annular processing chamber, such as processing chamber 45. The feed stream must be fed at an appropriate rate when using a system as shown in FIG. 12. If the feed stream rate is too large, then the velocity above the feed port 131 in the upper product section of the chamber will potentially be too great to allow even the more mobile molecules to pass counter-currently downward. This limitation on feed rate can be remedied using the system of FIG. 13 as will be explained more fully below. The particular limitations on feed rate depend upon a variety of factors which are specific to the processor geometry and chemical system being used.

The process further includes establishing an electrical field having a voltage gradient which varies along the longitudinal length or axis of the annular processing chamber. The electrical field strength can vary over a wide range of values as is well known in the art of electrophoretic processing. Typically the field strength will be in the range of 20–100 volts per centimeter. In general with the preferred processors described herein, the electrodes are charged to voltages which provide a differential voltage therebetween which are typically in the range of 1000–2000 volts.

The process also includes including a transverse secondary flow of the process fluid. This inducing step is significant in improving heat transfer and reducing the ill effects of electroosmosis which tends to create longitudinal fluid currents in the process fluid along the chamber surfaces. These ill effects are caused by electrical charge development along the surfaces of the processing chamber, as is recognized and described in the art.

The inducement of a transverse secondary flow is preferably accomplished by rotating a rotor, such as rotor 50, having surfaces which at least partially define the processing chamber. The rotational speed is of sufficient magnitude to induce a transverse secondary flow of the process fluid which reduces the longitudinal migration of mobile molecules contained therein. The rotation is preferably done at sufficient rotational velocity to induce toroidal laminar secondary flow cells which are called Taylor vortices.

Figure 15:
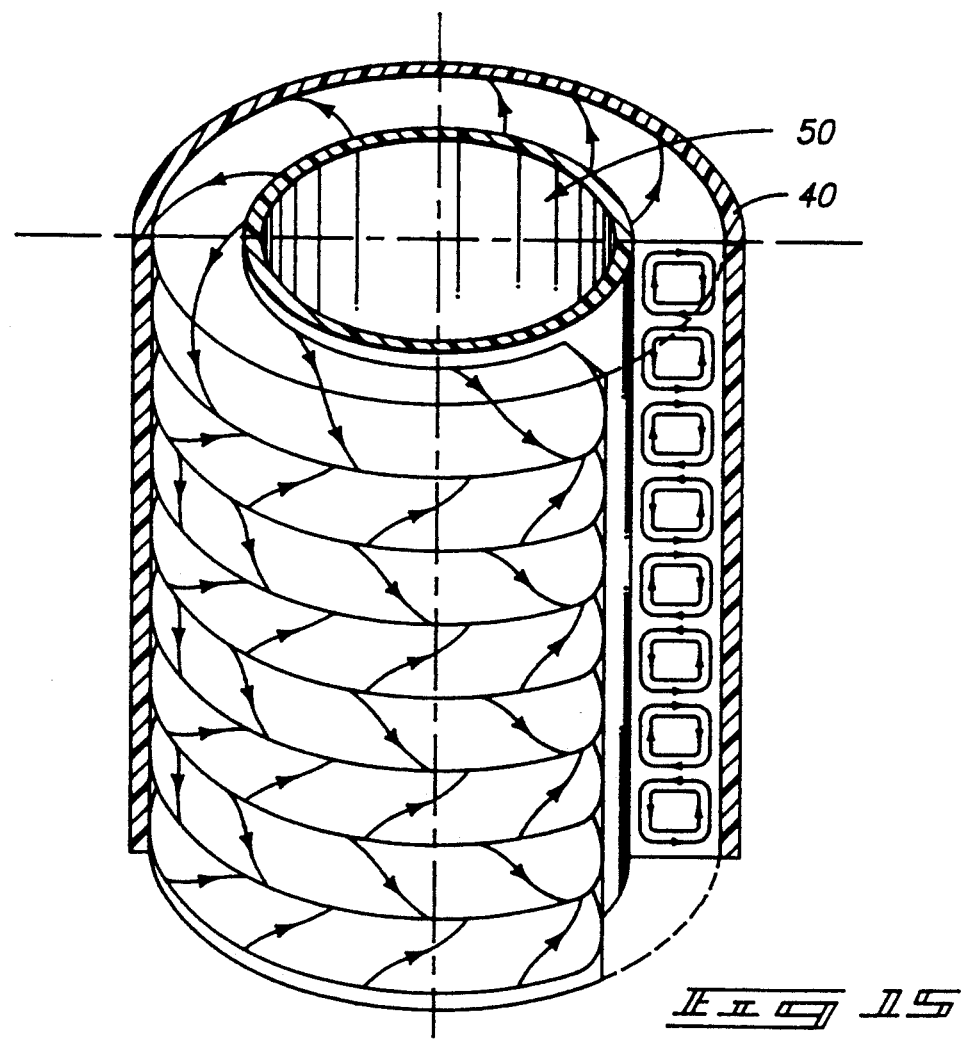
FIG. 15 is a diagram generally showing the toroidal secondary flows or Taylor vortices preferably developed by the processor.

Taylor vortices are diagrammatically shown in FIG. 15. The toroidal vortices spiral transversely between the stator and rotor at a plurality of longitudinal positions. Each Taylor vortex cell is approximately square in cross-sectional size as determined by the annular processing chamber gap size 53. A circulating laminar flow of processing fluid spirals through the cell as illustrated in a spiraling donut appearance.

The angular speeds needed to generate the Taylor vortices varies dependent upon fluid properties (primarily kinematic viscosity), process chamber gap, and radius of the inner cylinder. This has been represented in theoretical work on Taylor vortex development. The flow conditions relevant to Taylor vortex development are represented by the Taylor number, T, which is defined as:

$$T = (R^3 fD/\nu)$$

where: f is the rotational frequency; R is the radius of the inner cylinder; $\nu$ is the kinematic viscosity; and d is the annular gap. Flows having Taylor numbers within a critical range typically induce Taylor vortices. The lower critical Taylor number, $T_c = 1708$, results in the generation of Taylor vortices. The upper critical Taylor number is approximately 3025, but the value is a complex function highly dependent on apparatus geometry. Both of these numbers apply to the preferred embodiment geometry and sizes set forth in this application.

Figure 14:
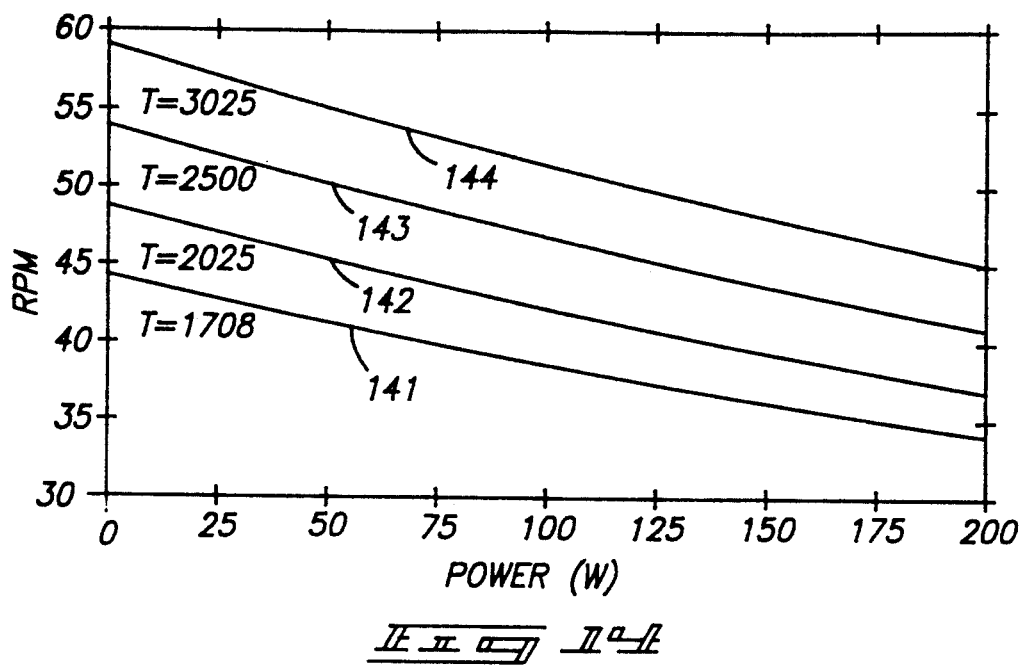
FIG. 14 is a graph showing rotor angular velocities used to achieve Taylor vortices as a function of power input to the system.

FIG. 14 is a graph showing appropriate Taylor numbers on the lines labeled 141–144 for a particular processor having a stator diameter of 10 cm and a rotor diameter of 9.67 cm. The corresponding Taylor numbers are 1708, 2025, 2500, and 3025, respectively. Taylor vortices are typically formed with a processor of the type and size described above when the Taylor numbers range from approximately 1708 to 3025. At Taylor numbers below 1708 the flow does not typically develop into the characteristic toroidal vortex and a Couette flow regime is established which is not as effective for use in the processing described herein. At Taylor numbers above 3025 the flow typically becomes turbulent. Turbulent flow is undesirable because it causes excessive mixing and prevents the desired separation. Thus the inducing and rotating processing steps can be effectively accomplished by rotating at an appropriate angular speed to create transverse toroidal secondary flows of the Taylor vortex type.

For a variety of processor geometries, the preferred rotational speeds are typically in the range of 10–400 revolutions per minute, more preferably 30–100 revolutions per minute.

The processing advantageously accomplished by the system illustrated by FIG. 12 also includes flowing a counterflow of processing fluid or other working fluid through the processing chamber in a direction generally longitudinal and in opposition to migration of at least one of the electrophoretically mobile chemicals contained in the process fluid. This is advantageously accomplished by pumping a suitable buffer into the processing chamber, such as through the primary working fluid port 88. The counterflowing fluid preferably moves from the bottom of the annular processing chamber upwardly. The counterflow of fluid through the processing chamber is at a rate appropriate to sweep the less mobile molecules upwardly against the electrical field established. The counter flow is also preferably at a rate appropriate to allow the more mobile molecules to move downwardly along the processing chamber as forced by the electrical field produced, such as by electrodes 98.

The zone focusing electrophoretic processes of this invention also preferably involve varying the counterflow velocity along the length of the processing chamber. The velocity changes along the processing chamber allow the counterflow to selectively sweep molecules of a given mobility to a desired position or zone. The velocity change at a particular point is effected by outflowing a portion of the counterflow, such as by outflowing at higher mobility port 123. The velocity between port 123 and port 131 thus is approximately constant and of a speed which allows the higher mobility molecules to move to port 123. However, the velocity between ports 123 and 131 is high enough to prevent the lower mobility molecules which are being separated from progressing to port 123.

The counterflow velocity between port 131 and 127 can be either greater than or equal to the velocity between ports 123 and 131. During continuous flow operation the feed port supplies fluid and the velocity between ports 131 and 127 will be higher on average than the velocity between ports 123 and 131. This is an undesirable velocity profile but is acceptable for simplicity purposes. The higher velocity in the upper section is acceptable until it prevents the more mobile molecules from being forced by the electrical field between ports 127 and 131. Under such conditions the sample feed flow rate must be reduced or an alternative system used as explained below.

FIG. 13 shows an alternative system which is provided with additional components which remedy the potential problems associated with a significantly higher counterflow velocity in the upper section of the processing chamber. The system of FIG. 13 is similar to that shown and described with respect to FIG. 12 and the same reference numerals have been used for similar parts. The system of FIG. 13 also includes an infeed recycle port 132 which is positioned along approximately the same longitudinal position as the feed port 131. A feed recycle pump 138 is used to control the recycle flow rate out through port 132. Pump 138 is also preferably a peristaltic tubing pump. The outlet of pump 138 is fed to the first side 139 of an ultrafilter 137. Ultrafilter 137 is of sufficiently small pore size so as to retain the molecules which are being separated. The second side 140 of filter 137 is connected to a pump 150 which is used to remove sufficient working fluid from the recycle line to effectuate the desired net flow increase, decrease or equality desired at the medial section of the processing chamber. The net flow is decreased by removing with pump 150 fluid at a rate in excess of the sample feed rate provided by pump 133. The converse applies if a net flow increase is desired. If no net effect is desired then the flows through ports 131 and 132 are balanced.

The velocity in the upper section of the processing chamber can thus be adjusted by varying the feed inflow through port 131 and the feed recycle outflow which occurs through port 132. If these flows are made equal, then the processing chamber longitudinal counterflow velocity is equal between ports 123 and 127. If there is a net outflow at the feed section then the counterflow velocity above ports 131 and 132 is generally decreased. If there is a net inflow, then the counterflow velocity above ports 131 and 132 increases as was the case in the system of FIG. 12.

The novel processes for continuous electrophoretic separation processing further include removing at least two outflow streams containing the fractions being separated. This is advantageously done through the upper and lower product ports 127 and 123 which carry the relatively low mobility and high mobility fractions, respectively.

EXAMPLE 1

Continuous flow zone electrophoretic processing was performed in a processor as described above in connection with processor 20. Chilled water at 2° C. was used as cooling media and circulated through the cooling jacket chamber 44. The medium size rotor was employed. A mixture of approximately 1% bovine albumin and 1% bovine hemoglobin in an aqueous buffer solution was prepared using commercial sources of these chemicals. The buffer solution was 20 mM tris-acetate at pH 8.0. The albumin was rendered visible by dyeing with bromophenol blue prior to injection into the processing chamber. The mixture was fed at a rate of 15 milliliters per hour using a system similar to that shown in FIG. 12. The counterflow of buffer was approximately 40 milliliters per hour. The electrodes were charged to a differential voltage of 1350 volts. The albumin separated as the higher mobility product through port 123 and the hemoglobin separated as the lower mobility product through port 127. No cross-contamination was detected in either resulting product stream.

The invention further includes processes for batch electrophoretic separation of chemical constituents having differing electrophoretic mobilities. The batch electrophoretic zone processing described herein is not a true batch process in that a working fluid, such as a buffer, is counterflowed through the processing chamber. However, the reference to batch processing relates to the use of a single sample charge which is fed into the processing chamber in a charging operation. The electrophoretic zone processing then proceeds with time upon the sample charge to separate the electrophoretically mobile components in one or more zones along a counterflow having a varying velocity profile.

The batch electrophoretic zone processing can be performed using the system illustrated in FIG. 13. The process includes feeding an approximately annular processing chamber, such as processing chamber 45. The feeding is performed upon a fixed sample over a period of time to thereby perform charging of the processing chamber with the sample and any suitable carrier fluid in which the sample is carried. Feeding and charging of the sample is accomplished in the system of FIG. 13 by pumping the sample using pump 133 and feeding the sample fluid into the processing chamber 45 through the sample infeed port 131. The sample charging is preferably done while also counterflowing the working fluid through the processing chamber as described hereinabove.

The batch zone processes of this invention further include establishing an electrical field as described hereinabove in connection with the continuous flow zone electrophoresis separation processes. Similarly, the rotating and inducing of secondary flows are similar to those described above.

The batch zone processes further include varying the counterflow velocity along the length or longitudinal axis of the processing chamber to focus at least one of the mobile chemicals within a zone. The zone or zones are typically provided at a position along the processing chamber whereat the counterflow velocity changes due to the removal of working fluid. For example, at the medial position where fluid can be removed at the recycle port 132 using pump 138 and 150. In such an operation a flow restricting valve 153 can be included to separate the feed port 131 and removal port 132. In this operation the processing chamber is thus provided with a velocity profile which decreases upwardly. The final step of velocity decrease is between the upper product port 127 and port 89 wherein the velocity becomes very low and the electrical field tends to move all mobile constitutents of the process fluid downwardly.

The batch zone processing tends to focus the desired protein or other chemical in a desired zone. For example the system can be operated to focus a single constitutent being sought along the medial section. After sufficient time has passed for the desired constituent to be separated into the medial zone, then the process further includes removing fluid from the zone of the processing chamber to obtain the chemical fraction which has been separated. Thus the processing chamber is charged with the initial sample containing a variety of constituents and the processed fluid retains the single or multiple constituents desired having appropriate mobilites to selectively retain or focus them at the point in the processing chamber at which electric field mobility and counterflow velocity are in balance.

EXAMPLE 2

Batch zone electrophoretic processing was performed in a processor as described above in connection with processor 20. Chilled water at 2° C. was used as cooling media and circulated through the cooling jacket chamber 44. The medium size rotor was employed. A mixture of approximately 1% bovine albumin and 1% bovine hemoglobin in an aqueous buffer solution was prepared using commercial sources of these chemicals. The buffer solution was 20 mM tris-acetate at pH 8.0. The albumin was rendered visible by dyeing with bromophenol blue prior to injection into the processing chamber. The mixture was fed at a rate of 23.2 milliliters per hour using a system similar to that shown in FIG. 13. Recycle flow from port 132 was 19.6 milliliters per hour. The net feed was 3.6 milliliters per hour. The sample was fed during an initial charging period of about 20 minutes duration. The counterflow of buffer was varied from approximately 60 milliliters per hour to 100 milliliters per hour during the period of separation. The electrodes were charged to a differential voltage of approximately 1600 volts. The albumin was separated into the medial zone as the higher mobility product. The hemoglobin separated as the lower mobility product exiting through port 127 in the counterflow stream. The batch separation process proceeded for about 3 hours. The albumin containing process liquid was removed by draining the processing chamber.

The processors of FIGS. 10 and 11 are specifically adapted to facilitate operation in an isoelectric focusing mode of operation and description of this mode of operation will be made with reference to these Figures. The isoelectric focusing mode of operation includes charging processing chamber 45 with a isoelectric process fluid containing at least two chemicals which have differing electrophoretic mobilities. These chemicals are often proteins or can alternatively be other electrophoretically mobile components being separated. The isoelectric process fluid also contains a suitable ampholyte mixture which causes a pH gradient to be established in response to the voltage gradient applied when the electrodes 98 are charged to the desired differential voltages.

The isoelectric focusing modes and methods also include establishing an electrical field having a voltage gradient varying along said longitudinal axis of the processing chamber 45. The electrical field established can be of either polarity. Establishing the electrical field within the ampholyte containing isoelectric process fluid results in creating a pH gradient having a range of pH conditions within the processing chamber fluid. Creating a pH gradient within the processing chamber fluid chamber allows the electrophoretically mobile chemical constituents of the isoelectric processing fluid to separate at different longitudinal positions where the pH is equal to the isoelectric point of the particular constituent.

The separating step is preferably accomplished while rotating the rotor 40. Rotor 40 is preferably rotated at angular speeds sufficient to generate annular Taylor vortices in the processing chamber for the particular rotor size being employed. The developing or generating of the annular Taylor vortices helps to prevent electroosmosis during processing, improves heat transfer with the stator and rotor to allow heat removal or other temperature stabilization. Generating Taylor vortices also helps to prevent vertical convection currents from developing. Convection currents which can otherwise develop are derogatory to the isoelectric focusing of the constituent chemicals at the appropriate isoelectric pH location. The Taylor vortices generated help prevent large scale convective currents from mixing the isoelectric process fluid and maintain focused bands in relatively homogeneous condition.

In this approach the electrodes 98 are charged to the desired potentials using any power supply suitable to generate the desired voltages at the electrodes and maintain the electrodes at the desired differential voltages as current flows between the electrodes across the processing chamber. Such current flows as a result of the pressure of charge carriers in the processing fluid.

In general the polarity of the chemicals being electrophoresed and the polarity of the electrical field established by electrodes 98 is coordinated so that the electrical field force exerted upon the chemicals is downward in the processors described herein.

EXAMPLE 3

Batch isoelectric electrophoretic processing was performed in a processor as described above in connection with processor 20. Chilled water at 2° C. was used as cooling media and circulated through the cooling jacket chamber 44. The medium size rotor was employed. A sample containing 10 milligrams of bovine albumin and 10 milligrams bovine hemoglobin in an aqueous buffer solution was prepared using commercial sources of these chemicals. The albumin was rendered visible by dyeing with bromophenol blue prior to injection into the processing chamber. The buffer solution was formed from deionized water and contained 2% Pharmalyte 3-10 ampholyte mixture (Pharmacia Brand). The albumin and hemoglobin were mixed with approximately 60 milliliters of such buffer and the resulting process fluid was fed into the processing chamber by pumping in from the bottom using a pump such as pump 121 described in FIGS. 12 and 13. The power supply was operated in the constant power mode at 100 watts. The initial voltage was 1000 volts. The separation processing was performed for approximately 45 minutes. Each constituent formed a band or zone approximately 2.4 centimeters high. A central band or zone approximately 6 centimeters high without color was present between the focused bands of protein. The zones of protein had estimated mean concentrations of 0.2% protein. More concentrated zones within the broader bands were estimated to have protein concentrations of approximately 1%.

Processor 420 of FIGS. 16 and 17 is specifically adapted to facilitate operation in a zone electric field gradient focusing mode of operation and description of this mode of operation will be made with reference to FIGS. 16 and 17. In zone electric field gradient focusing, electrophoretic chemicals are processed in an environment of changing electric field strength. The counterflow of fluid is maintained at an appropriate rate, which can very or more preferably is approximately constant rate.

According to this method, a multi-zone or positionally varying electric field is produced within processing chamber 53, 53'. Each zone most preferably has a different field strength and is established between associated, neighboring pairs of electrodes 98 and 422–424. A first electric field zone is defined by top electrode 98 and electrode 422. A second electric field zone is defined by electrodes 422 and 423. A third electric field zone is defined by electrodes 423 and 424, and a fourth zone is defined by electrode 424 and bottom electrode 98.

The field strengths are controllable by adjusting the electric potential applied to the intermediate electrodes 422–424. This is accomplished by changing the resistances of potentiometers 438–442 (via controller 452 and drivers 444–448) of voltage divider 436. An approximate step change in the electric field strength can be provided at each intermediate electrode. More preferably, the field strength of the associated zones decrease from the upper zone between top electrode 98 and intermediate electrode 422 to the lower zone between intermediate electrode 424 and bottom electrode 98, although other arrangements are possible. The multi-zone electrical field is thereby oriented to cause an electrophoretic force to be developed upon the molecules to drive them in a downward direction from the top of the processing chamber to the bottom.

A counterflow of fluid is established in an upward direction from the bottom of the processing chamber to the top. The fluid is introduced at inflow port 454 and removed through outflow port 456. Controller 452 governs flow rate and volume via values 460 and 462. This counterflow can advantageously be provided at a constant flow rate.

Processor 420 is suitable for concentrating samples of one chemical or separating samples of two or more chemicals. Where a sample having one chemical is introduced into processing chamber 53, the counterflow of fluid tends to move the molecules of that chemical in an upwards direction, whereas the various electric fields tend to move the molecules in a downwards direction. According to this invention, the opposing forces upon the molecules are balanced to focus the molecules within a region or zone of the chamber. That is, the molecules will focus at a location where the force induced by the counterflow is canceled and thus neutralized by the counteracting electrophoretic force induced by the various electric fields. Such focusing may occur, for example, in an electric field zone between intermediate electrodes 422 and 423. Concentrations of the chemical can then be removed via one or more ports 327–332 (or representative port 458 of FIG. 17) positioned between these two intermediate electrodes.

Where more than one chemical is involved, the process of this invention effectively separates the chemicals into separate and substantially distinct focusing regions or zones. For instance, for a sample of two chemicals, one chemical may be focused between intermediate electrodes 422 and 423 and the other chemical may be focused between intermediate electrode 424 and bottom electrode 98. In this manner, concentrations of the first chemical can be extracted through ports 327–332 and concentrations of the second chemical can be extracted through ports 339–345.

It is also possible using the processor of FIGS. 16 and 17 to vary the field strengths with time during the processing cycle. Controller 452, drivers 444–448, and potentiometers 438–442 afford this flexibility. According to an aspect of this invention for separating two or more chemicals, multi-zone electric field generator 421 produces field strengths in the respective zones having first field gradients that are relatively steep during an initial phase of the processing cycle. The generator then produces field strengths of second field gradients that are less than the first field gradients, or relatively flat, during a second subsequent phase of the processing cycle. During yet a third subsequent phase of the processing cycle, the generator can once again produce field gradients that are relatively steep. This controlled process provides an efficient and effective method for separating two or more chemicals. It is believed that this process is capable of resolving solutes whose electrophoretic mobilities differ by as little $10^{-5}$ cm$^2$/V-s, corresponding to about one charge group on a protein.

The zone electric field focusing mode is advantageous in that it provides a relatively rapid separation of materials. Unlike the pH gradient in isoelectric focusing, the different electric field strengths are established immediately at the start of the experiment. The method is both gentle and flexible because focusing can be carried out in arbitrary buffer and solvent compositions, neutral pH, physiological ionic strengths and with both ionic and nonionic additives.

EXAMPLE 4

A test was conducted using a processor similar to that discussed above with reference to FIG. 16, but modified to have only one centrally located intermediate electrode, such as electrode 424. The stator was constructed of PLEXIGLAS tube having a one-inch inner diameter. An aluminum rotor having a 7/8-inch outer diameter, and insulated with 0.015-inch heat-shrink TEFLON tubing, was mounted concentrically within the stator to form an annulus having a length of 25 cm with a 1/16-inch gap. A first electrode, or primary cathode, was mounted on the top of the annulus, and a second electrode, or primary anode, was mounted at the bottom of the annulus. A third electrode was placed intermediate of the cathode and anode near the center of the annulus.

Deionized, degassed water chilled to 4° C. was used as cooling media and circulated through the cooling jacket chamber 44. The buffer was degassed for five minutes under 600 mm Hg vacuum. Bovine serum albumin (BSA) was labeled with bromophenol blue (Sigma) by adding dye, typically a 2:1 molar ratio, from a stock solution with a concentration of 1 mg/ml to 100 mgs of BSA. After dyeing, the protein solution was diluted to 5 ml in buffer and then either passed through a size-exclusion column containing a mixed bed of G-10 and G-25 equilibrated against running buffer or dialyzed against two changes of buffer overnight. This dye gave BSA a distinct blue color with an isolated absorption peak in the visible range at 610 nm.

The annulus was precharged with 50 mg of dye-labeled BSA diluted to 30 mls using 10 mM Trisphosphate buffer at pH 7.5. The rotor was accelerated to 80 RPM to generate Taylor vortices. A voltage of 2000 V was applied to the cathode on top of the annulus, and the cathode and third electrode were grounded. This produced a nominal electric field strength of roughly 200 V/cm in the upper half of the chamber above the third electrode and no electric field in the lower half of the chamber below the third electrode. A step change in the electric field occurred near the third electrode.

After turning on the electric field, crossflow of approximately 0.5 ml/min (approximately 0.5 cm/min) was introduced at the base of the annulus near the anode and allowed to flow axially upward through the annulus. It was observed that in the lower half of the chamber, between the anode and third electrode, the crossflow swept the protein toward the center of the chamber. In the upper half of the chamber, the electric field drove the electrophoretic migration of BSA toward the center of the chamber against the opposing counterflow. This combined migration pattern focused the protein near the central, third electrode. The BSA was held in the central portion of the chamber for more than three hours at a concentration of roughly 2 mg/ml before the electric field was turned off and the protein was washed from the chamber.

Processors 520 and 700 of FIGS. 18 and 19 are other apparatuses suitable for facilitating a zone electric field gradient focusing mode of operation. Because they function substantially similarly, description of this mode of operation will be made with reference to processor 520 of FIG. 18. According to this method, voltages are applied to electrodes 528–532 to establish processing zones of different electric field strengths within compartments 560–564. Preferably, the field strengths decrease from top compartment 560 to bottom compartment 564 to define a field strength gradient profile that tends to force molecules downward in chamber 522.

A counterflow of fluid is established from the bottom of processing chamber 522 to the top which tends to force molecules upward. The counterflow force counteracts the electrophoretic force such that these forces are balanced within various compartments for differently charged chemicals. In this manner, the chemicals are focused or concentrated into compartments 560–564 and can be extracted therefrom through associated ports 552–556.

The zone electric field gradient focusing mode of operation carried out within the stacked membrane processor 520 is advantageous because the solute focuses into a single compartment with small amounts of material dispersed into adjacent compartments. Additionally, it is believed that the process is fast, taking only about one minute to come to its final state. The rapidity of this process is because the solute only needs to migrate through a very thin membrane (e.g., 100 $\mu$m) in order to pass from one compartment to the next. The electric potential change between two adjacent compartments occurs over a very short distance and thus the electric field within the membrane pores can be very large (e.g. 1,000 V/cm). The process can be accelerated by using thinner membranes, larger potential differences, and thinner compartments. It is believed that the process is capable of resolving solutes with electrophoretic mobilities that differ by less than 2%.

EXAMPLE 5

A mathematically simulated computer test was conducted using a model representative of a processor similar to that shown in FIG. 18, but modified to have six compartments. Five identical electroultrafiltration membranes were employed, each 100 $\mu$m thick and having a porosity of 0.1. The compartments were 1 cm in depth.

Electric potentials of 36, 25, 16, 9, 4, and 1 volts were applied respectively to the six electrodes. A solute having electrophoretic mobility of $10^{-5}$ $cm^2$/V-s was initially loaded into the lowest voltage setting (i.e., 1 volt). A counterflow of fluid was established within the chamber at 1 cm/min in a direction opposing the force induced by the electric fields.

Once the crossflow was started, the solute moved out of the first compartment, through the second compartment, and focused in the third compartment. Only a small fraction of solute was detected in the adjacent second and fourth compartments.

EXAMPLE 6

A Vortophor was constructed along the principles discussed for processor 600. The apparatus was inverted with respect to FIG. 20, the shaped wall 654 being closest together at the bottom of the apparatus and buffer flow in the working space being from top to bottom. Walls 654 were straight and parallel, with a step change in their separation at the midpoint of the apparatus. The distances between walls 654 were chosen so that the electric field would be 15% greater in the lower half of the apparatus. With the buffer flow downward from top to bottom in the working space, the electrode polarity was arranged so that the protein of interest would electrophorese upward, and be held at the field step when the electric fields and buffer flow were suitably balanced.

Bovine albumin and bovine hemoglobin were separated in an example separation in this processor. The buffer contained 40 mM tris base [tris(hydroxymethyl)aminomethane] and sufficient glycine to bring the pH to 8.0. The albumin was dyed with bromophenol blue to render it visible and clearly distinct photometrically from hemoglobin. The feed consisted of 60 mg hemoglobin and 100 mg dyed albumin in 11.5 ml buffer. A sidestream was taken from the working space at the field step, pumped through a spectrophotometer to allow continuous monitoring of the separation, and returned to the working space at the field step. The Vortophor rotor was rotated at 60 rpm. The buffer flow in the working space was 1 ml/min. The feed solution was injected into the working space at the field step at the rate of 0.16 ml/min. It was found that the electrical fields set up by passage of 25 mA current sufficed to hold the albumin at the field step, while the hemoglobin was washed out of the working space through a port corresponding to 462 in FIG. 20.

It should further be appreciated that various features shown in the processors can be combined and mixed in various combination consistent with the teachings contained herein. Similarly, the various processing steps and techniques can in most instances be applied in varied combinations to utilize specific features or advantages resulting from such combinations. Thus the technical support provided by this specification includes combinations of the described processors and processing methods although not specifically set forth herein.

In compliance with the statute, the invention has been described in language necessarily limited in its ability to properly convey the conceptual nature of the invention. Because of this inherent limitation of language, it must be understood that the invention is not necessarily limited to the specific features described, since the means herein disclosed comprise merely preferred forms of putting the invention into effect. The invention is, therefore, claimed in any of its forms or modifications within the proper scope of the appended claims appropriately interpreted in accordance with the doctrine of equivalents.

We claim:

1. An electrophoretic processor comprising:
    a stator;
    a rotor mounted for rotation about an axis of rotation;
    a rotor drive for rotating said rotor;
    a processing chamber at least partially defined between the stator and rotor;
    multi-zone electric field generator for creating at least two processing zones having different field strengths within the processing chamber;
    at least one fluid access port allowing fluid communication to or from said processing chamber.

2. An electrophoretic processor according to claim 1 wherein the multi-zone electric field generator comprises:
    a first electrode positioned adjacent a first end of the processing chamber;
    a second electrode positioned adjacent a second end of the processing chamber;
    a third intermediate electrode positioned between the first and second electrodes.

3. An electrophoretic processor according to claim 1 wherein the multi-zone electric field generator comprises:
    a first electrode positioned adjacent a first end of the processing chamber;
    a second electrode positioned adjacent a second end of the processing chamber;
    a plurality of intermediate electrodes positioned between the first and second electrodes.

4. An electrophoretic processor according to claim 1 wherein the multi-zone electric field generator includes a variable field control system which allows the various field strengths of the processing zones to be adjusted.

5. An electrophoretic processor according to claim 1 wherein the multi-zone electric field generator comprises:
    a first electrode positioned adjacent a first end of the processing chamber;
    a second electrode positioned adjacent a second end of the processing chamber;
    a third intermediate electrode positioned between the first and second electrodes;
    variable resistive elements electrically coupled between the first and third electrodes and between the second and third electrodes;
    a resistance control system connected to the variable resistive elements for adjusting the variable resistive elements to control the various field strengths of the processing zones.

6. An electrophoretic processor according to claim 1 wherein there are a plurality of fluid access ports.

7. An electrophoretic processor according to claim 1 and further comprising a moveable catheter for extracting fluid from a plurality of locations within the processing chamber.

8. An electrophoretic processor according to claim 1 wherein said rotor drive is a magnetic coupling.

9. An electrophoretic processor according to claim 1 wherein said rotor comprises an adjustable rotor assembly which is adjustable to allow multiple rotor sizes to provide various sized spacings between the stator and the rotor.

10. An electrophoretic processor according to claim 9 wherein the adjustable rotor assembly includes multiple interchangeable rotors of different cross-sectional diameters.

11. An electrophoretic processor comprising:
    a processing chamber having an axis;
    an inflow port allowing fluid communication to the processing chamber,
    an outflow port allowing fluid communication from the processing chamber, the outflow port being axially spaced from the inflow port;
    multi-zone electric field generator for creating at least two processing zones having different field strengths within the processing chamber;
    wherein the multi-zone electric field generator comprises;
    a plurality of electrodes axially spaced along the processing chamber;
    variable resistive elements electrically coupled between adjacent electrodes;
    a resistance control system connected to the variable resistive elements for adjusting the variable resistive elements to control the various field strengths of the processing zones.

12. An electrophoretic processor comprising:
    a processing chamber having an axis;
    an inflow port allowing fluid communication to the processing chamber;
    an outflow port allowing fluid communication from the processing chamber, the outflow port being axially spaced from the inflow port;
    multi-zone electric field generator for creating at least two processing zones having different field strengths within the processing chamber;
    at least one permeable membrane disposed within the chamber transverse to the axis.

13. An electrophoretic processor comprising:
    a processing chamber having an axis;
    an inflow port allowing fluid communication to the processing chamber;
    an outflow port allowing fluid communication from the processing chamber, the outflow port being axially spaced from the inflow port;
    multi-zone electric field generator for creating at least two processing zones having different field strengths within the processing chamber;
    a plurality of electrodes axially spaced along the processing chamber;
    a plurality of permeable membranes disposed within the chamber transverse to the axis and interposed between at least one pair of adjacent electrodes.

14. An electrophoretic processor comprising:
    a processing chamber having an axis;
    an inflow port allowing fluid communication to the processing chamber;

an outflow port allowing fluid communication from the processing chamber, the outflow port being axially spaced from the inflow port;

multi-zone electric field generator for creating at least two processing zones having different field strengths within the processing chamber;

a moveable catheter for extracting fluid from a plurality of locations within the processing chamber.

15. A process for electrophoretically processing, comprising:

introducing a sample having at least one chemical which displays electrophoretic mobility within a processing chamber;

establishing a flow of carrier fluid in a first direction within the processing chamber;

producing within the processing chamber a multi-zone electrical field which has at least two processing zones with different electrical field strengths; said multi-zone electrical field being oriented to cause an electrophoretic force to be developed upon molecules of said at least one chemical which is in opposition to said first direction.

16. A process according to claim 15 and further comprising balancing opposing forces upon molecules of said chemical which occur due to said electric field and said flow of carrier fluid to thereby focus molecules of said chemical within a region of said processing chamber.

17. A process according to claim 15 and further comprising removing concentrations of said chemical from the processing chamber which develop within a focusing region of the processing chamber to which molecules of said chemical tend to migrate.

18. A process according to claim 15 and further comprising varying the field strengths in relation to duration of process.

19. A process according to claim 15 and further comprising producing field strengths having a first field gradient during a first phase of the process and producing field strengths having a second field gradient less than the first field gradient during a subsequent second phase of the process.

20. A process according to claim 15 and further comprising:

producing field strengths having a first field gradient during a first phase of the process;

producing field strengths having a second field gradient less than the first field gradient during a subsequent second phase of the process;

producing field strengths having a third field gradient greater than the second field gradient during a third phase of the process that is subsequent to the first and second phases.

21. A process according to claim 15 and further comprising establishing the flow of carrier at a constant flow rate.

22. A process according to claim 15 wherein said processing chamber is a conduit.

23. A process according to claim 15 wherein said processing chamber is an annular conduit.

24. A process according to claim 15 wherein said processing chamber is an annular conduit and further comprising rotating a surface defining the annular conduit to produce transverse fluid flows within the processing chamber.

25. A process according to claim 15 wherein said processing chamber is an annular conduit and further comprising rotating a surface defining the annular conduit to produce transverse Taylor vortices within the processing chamber.

26. A process according to claim 15 wherein said processing chamber is a conduit having at least one porous membrane disposed therein and aligned transversely to the flow of carrier, and further comprising passing the flow of carrier through the membrane.

27. A process for electrophoretically processing, comprising:

introducing a sample having at least two chemicals, first and second chemicals, which display differing electrophoretic mobilities within a processing chamber;

establishing a flow of carrier fluid in a first direction within the processing chamber;

producing within the processing chamber a multi-zone electrical field which has at least two processing zones with different electrical field strengths; said multi-zone electrical field being oriented to cause electrophoretic forces to be developed upon molecules of said first and second chemicals which are in opposition to said first direction.

28. A process according to claim 27 and further comprising balancing opposing forces upon molecules of said first and second chemicals which occur due to said multi-zone electric field and said flow of carrier fluid to thereby focus molecules of said chemicals within two substantially distinct first and second focusing regions of said processing chamber.

29. A process according to claim 27 and further comprising removing concentrations of said chemicals from the processing chamber which develop within two substantially distinct first and second focusing regions of the processing chamber; to which molecules of said chemical tend to migrate.

30. A process according to claim 27 and further comprising varying the field strengths in relation to duration of process.

31. A process according to claim 27 and further comprising producing field strengths having a first field gradient during a first phase of the process and producing field strengths having a second field gradient less than the first field gradient during a subsequent second phase of the process.

32. A process according to claim 27 and further comprising:

producing field strengths having a first field gradient during a first phase of the process;

producing field strengths having a second field gradient less than the first field gradient during a subsequent second phase of the process;

producing field strengths having a third field gradient greater than the second field gradient during a third phase of the process that is subsequent to the first and second phases.

33. A process according to claim 27 and further comprising establishing the flow of carrier at a constant flow rate.

34. A process according to claim 27 wherein said processing chamber is a conduit.

35. A process according to claim 27 wherein said processing chamber is an annular conduit.

36. A process according to claim 27 wherein said processing chamber is an annular conduit and further comprising rotating a surface defining the annular conduit to produce transverse fluid flows within the processing chamber.

37. A process according to claim 27 wherein said processing chamber is an annular conduit and further comprising rotating a surface defining the annular conduit to produce transverse Taylor vortices within the processing chamber.

38. A process according to claim 27 wherein said processing chamber is a conduit having at least one porous membrane disposed therein and aligned transversely to the flow of carrier, and further comprising passing the flow of carrier through the membrane.

* * * * *